United States Patent [19]

Schadt et al.

[11] Patent Number: 5,447,657
[45] Date of Patent: Sep. 5, 1995

[54] LIQUID CRYSTAL COMPOUNDS

[75] Inventors: Martin Schadt, Seltisberg; Alois Villiger, Basel, both of Switzerland

[73] Assignee: Hoffmann-La Roche Inc., Nutley, N.J.

[21] Appl. No.: 208,165

[22] Filed: Mar. 8, 1994

Related U.S. Application Data

[63] Continuation of Ser. No. 107,554, Aug. 17, 1993, abandoned.

[30] Foreign Application Priority Data

Sep. 25, 1992 [CH] Switzerland .................. 3006/92

[51] Int. Cl.⁶ ................... C09K 19/52; C09K 19/34; C07D 239/02; C07D 319/06
[52] U.S. Cl. ................ 252/299.01; 252/299.61; 252/299.63; 252/299.66; 544/298; 544/335; 546/339; 546/346; 549/369; 549/374; 570/127
[58] Field of Search ............ 252/299.01, 299.61, 252/299.63, 299.66; 544/298, 335; 546/339, 346; 549/369, 374; 570/127

[56] References Cited

U.S. PATENT DOCUMENTS

| | | | |
|---|---|---|---|
| 5,068,053 | 11/1991 | Reiffenrath et al. | 252/299.61 |
| 5,164,114 | 11/1992 | Kurmeier et al. | 252/299.61 |
| 5,178,790 | 1/1993 | Weber et al. | 252/299.01 |
| 5,194,178 | 3/1993 | Coates et al. | 252/299.63 |

FOREIGN PATENT DOCUMENTS

| | | |
|---|---|---|
| 409634 | 1/1991 | European Pat. Off. |
| 4-5249 | 1/1992 | Japan . |
| 4-82854 | 3/1992 | Japan . |
| 5-65236 | 3/1993 | Japan . |
| 155465 | 9/1985 | United Kingdom . |

OTHER PUBLICATIONS

Adomenas et al., "Acetylenic liquid crystals available by Castro reaction", Chemical Abstracts, vol. 95:219871e, p. 494 (1981).

Derwent Abstract 89/138421/19 (1989) for DE 3 734 517.

Primary Examiner—Shean Wu
Attorney, Agent, or Firm—George M. Gould; George W. Johnston; Robert A. Silverman

[57] ABSTRACT

The present invention provides compounds of the general formula:

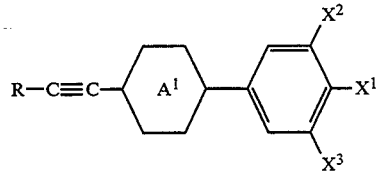

wherein
R is an alkyl group with 1 to 12 carbon atoms or a group of the formula

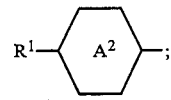

Ring $A^1$ is 1,4-phenylene, which is unsubstituted or substituted with fluorine, pyridine-2,5-diyl or pyrimidine-2,5-diyl;
Ring $A^2$ is trans-1,4-cyclohexylene or trans-1,3-dioxane-2,5-diyl;
$R^1$ is an alkyl, alkenyl or alkoxyalkyl group with 1 to 12 and, respectively, 2 to 12 carbon atoms;
$X^1$ is fluorine, chlorine, bromine, trifluoromethyl, trifluoromethoxy or difluoromethoxy; and
$X^2$, $X^3$ each independently are hydrogen or fluorine.

The invention is also concerned with liquid crystal mixtures which contain these compounds and with the use of these compounds and mixtures for electro-optical purposes.

16 Claims, No Drawings

LIQUID CRYSTAL COMPOUNDS

This is a continuation of application Ser. No. 08/107,554 filed Aug. 17, 1993, now abandoned.

BACKGROUND OF THE INVENTION

1. Field of the Invention

The present invention is concerned with liquid crystalline acetylene derivative, liquid crystalline mixtures which contain these compounds and their use for electro-optical purposes.

2. Background

Since the optical properties of liquid crystals can be influenced by an applied voltage, such substances are primarily used as dielectrics in indicating devices. Electro-optical devices based on liquid crystals are well-known to a person skilled in the art and can be based on various effects. The most common indicating devices are based on the Schadt-Helfrich effect and have a twisted nematic structure. Examples of such cells are TN cells ("twisted nematic") and STN cells (super-twisted nematic).

The liquid crystal materials for such cells must have a good chemical and thermal stability and a good stability towards electric fields and electromagnetic radiation. Further, the liquid crystal materials should have a low viscosity and in the cells should give short response times, low threshold potentials and a high contrast. At the usual operating temperatures they should have a suitable mesophase; for example, a nematic or cholesteric mesophase for the aforementioned cells. Further, the dielectric anisotropy should be as high as possible.

Since liquid crystals are usually used as mixtures of several components, it is also important that the components have a good miscibility with one another.

Liquid crystalline compounds which satisfy the aforementioned requirements are made available by the present invention.

SUMMARY OF THE INVENTION

The present invention provides compounds of the general formula:

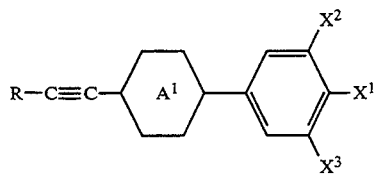

wherein
R is an alkyl group with 1 to 12 carbon atoms or a group of the formula

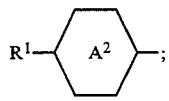

ring $A^1$ is 1,4-phenylene, which is unsubstituted or substituted with fluorine, pyridine-2,5-diyl or pyrimidine-2,5-diyl;
ring $A^2$ is trans-1,4-cyclohexylene or trans-1,3-dioxane-2,5-diyl;
$R^1$ is alkyl, alkenyl or alkoxyalkyl group with 1 to 12 or, respectively, 2 to 12 carbon atoms;
$X^1$ is fluorine, chlorine, bromine, trifluoromethyl, trifluoromethoxy or difluoromethoxy; and
$X^2$, $X^3$ each is independently hydrogen or fluorine.

DESCRIPTION OF THE PREFERRED EMBODIMENTS

The compounds in accordance with the invention are characterized by a high optical anisotropy. Their dielectric anisotropy is increased by the polar substituents on the phenyl ring. Further, these compounds have a remarkably low viscosity and a broad, favourable mesophase range as well as a comparatively high clearing point. All of these properties give rise to mixtures which contain compounds of general formula I having very good mesophases, and, moreover, a low threshold potential, short response times and a high contrast. The compounds of formula I are therefore especially suitable for use in TN and STN cells.

The term "alkyl with 1 to 12 carbon atoms" embraces straight-chain and branched (optionally chiral) alkyl residues such as, for example, methyl, ethyl, propyl, butyl, pentyl, hexyl, heptyl, octyl, nonyl, decyl, undecyl, dodecyl, 1-methylpropyl, 1-methylbutyl, 1-methylpentyl, 1-methylhexyl, 1-methylheptyl, 2-methylbutyl, 3-methylpentyl and the like. Especially preferred are straight-chain alkyl residues with 1 to 7 carbon atoms, but particularly those with 2 to 5 carbon atoms.

The term "alkenyl with 2 to 12 carbon atoms" embraces 1E-alkenyl, 3E-alkenyl, 4-alkenyl (E denoting the configuration of the double bond) or alkenyl having a terminal double bond and the like. Examples of such groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl (Z denoting the configuration of the double bond), 4Z-heptenyl, 5-hexenyl, 6-heptenyl, 7-octenyl and the like. Especially preferred are straight-chain alkenyl residues with 2 to 7 carbon atoms, but particularly those with 2 to 5 carbon atoms.

The term "alkyloxyalkyl with 2 to 12 carbon atoms" embraces groups such as, for example, methoxymethyl, methoxyethyl, methoxypropyl, methoxybutyl, ethoxymethyl, ethoxyethyl, ethoxypropyl, ethoxybutyl and the like. Preferred alkyloxyalkyl residues have 2 to 7 carbon atoms, especially 2 to 5 carbon atoms.

The term "1,4-phenylene, which is unsubstituted or substituted with fluorine," embraces 1,4-phenylene, 2-fluoro-1,4-phenylene and the like.

Preferred compounds of formula I are the bicyclic compounds of the formulas

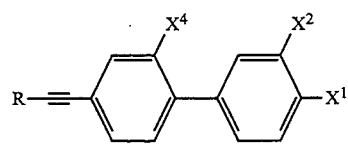

Ia

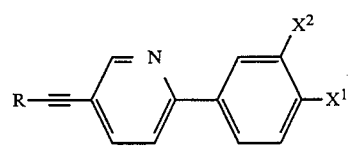

Ib

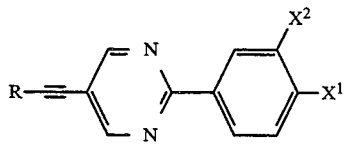

wherein R is an alkyl group with 1 to 12 carbon atoms; $X^1$ and $X^2$ have the meaning given above and $X^4$ is hydrogen or fluorine, as well as the tricyclic compounds of the formula

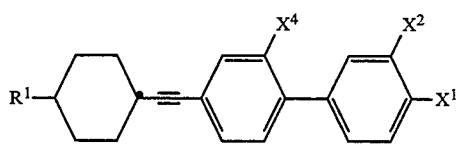

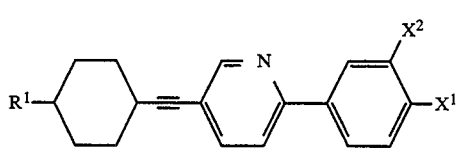

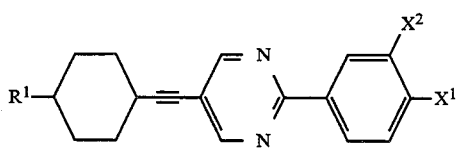

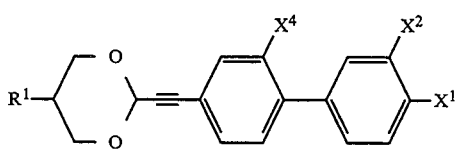

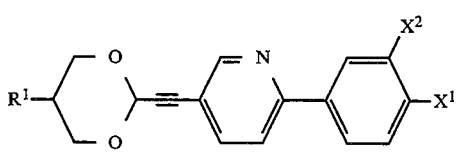

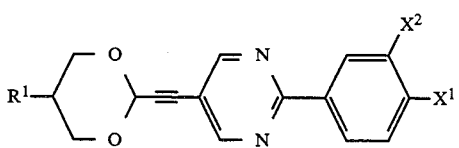

wherein $R^1$, $X^1$, $X^2$ and $X^4$ have the meanings given above.

The compounds of formulas Ia-Ii have a pronounced, broad nematic mesophase with a high clearing point. Especially preferred are the compounds of formulas Id-Ii, particularly those of formulas Id-If.

$X^4$ in the compounds of formulas Ia, Id and Ig preferably is for hydrogen.

The compounds of general formula I in which R is alkyl or trans-4-alkylcyclohexyl can be prepared in a manner known per se, e.g. according to the route illustrated in Scheme 1, i.e. by coupling a suitable acetylene derivative II with the corresponding bromo compound III in the presence of tetrakis(triphenylphosphine)palladium and CuBr. The reaction is preferably effected in triethylamine.

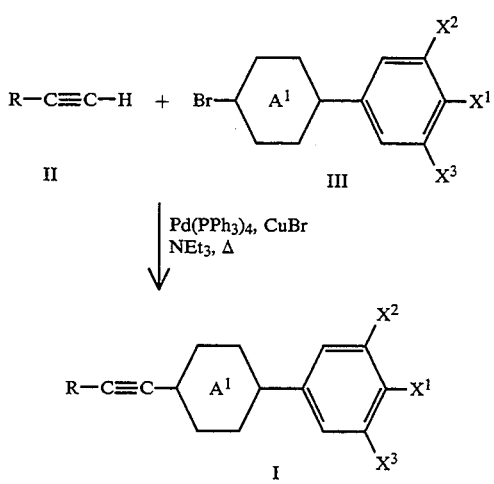

The bromo compounds used for the coupling with the acetylene derivatives can be prepared in a manner known per se, for example according to the route given in Scheme 2.

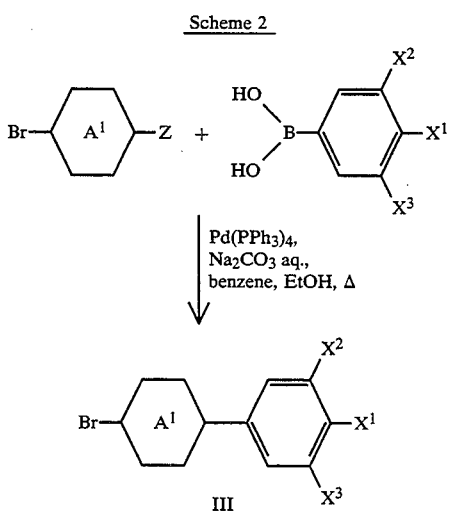

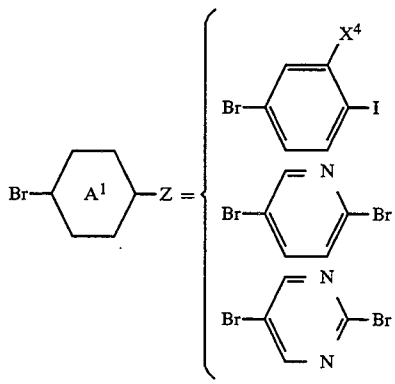

The tricyclic cyclohexylene derivatives of formulas Id-If in which $R^1$ is alkenyl or alkoxyalkyl can be prepared, for example, according to Scheme 3, i.e. by coupling a dioxaspiro[4,5]decaneacetylene derivative IV with the corresponding bromo compound III;

Scheme 3

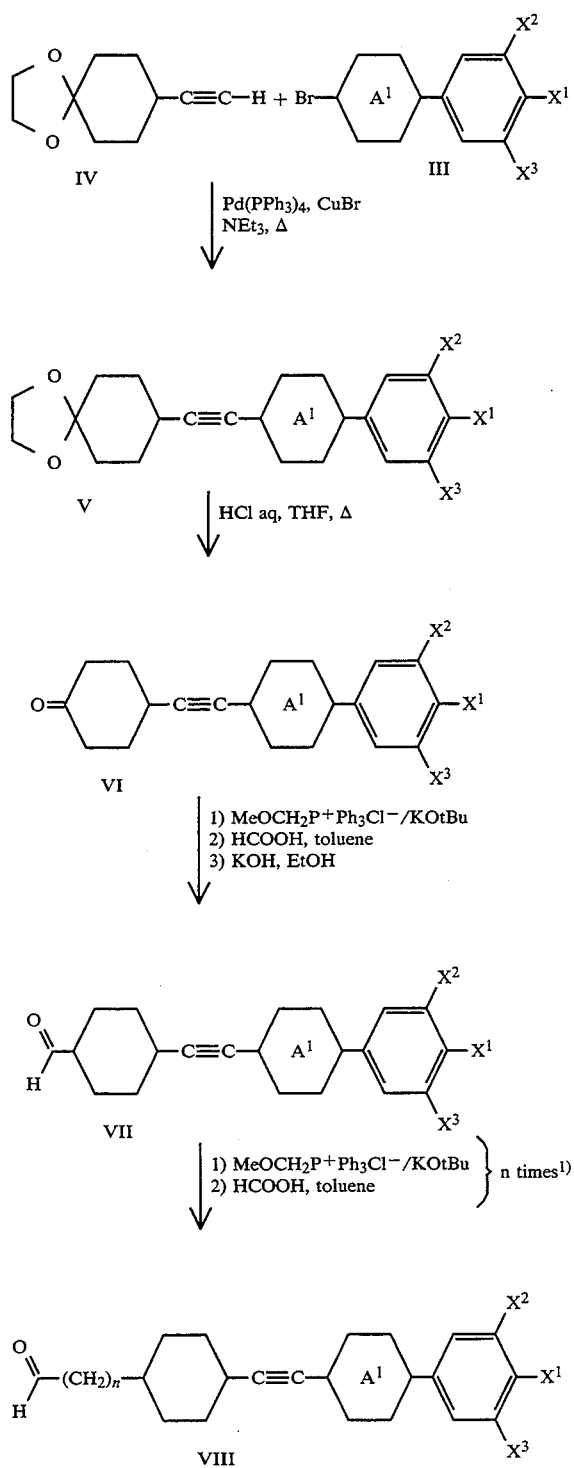

1) The reaction sequence is repeated n times depending on the chain length desired The side-chain $R^1$ can thus be synthesized by repeated homologization according to Wittig (see also Scheme 5).

The tricyclic dioxane derivatives of formulas Ig–Ii can be prepared, for example, according to Scheme 4, i.e. by coupling a suitable acetal-acetylene derivative IX and the corresponding bromo compound III and subsequently trans-acetalizing the compound X:

Scheme 4

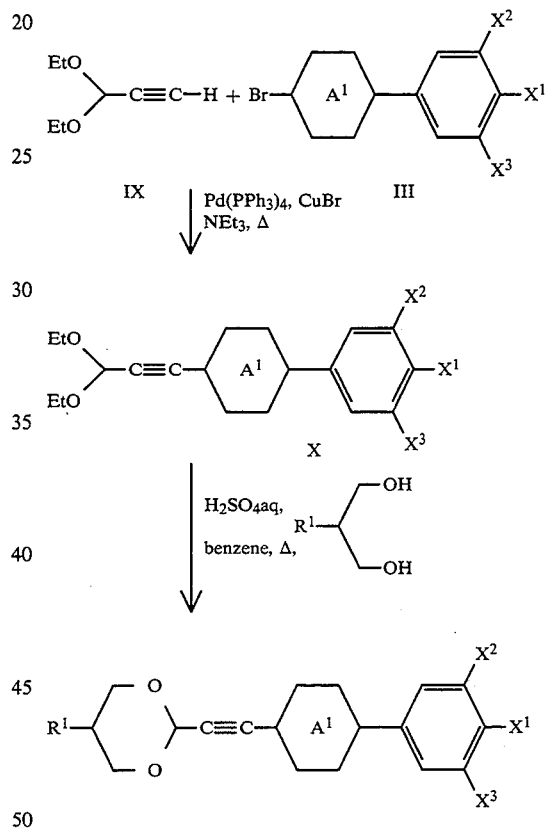

In the compounds of formula I in which $R^1$ is alkenyl, the double bond can be introduced in a manner known per se, e.g. in accordance with Scheme 5 from the corresponding aldehydes VIII by a Wittig reaction and subsequent isomerization.

In the compounds of formula I in which $R^1$ is alkyloxyalkyl, this residue can be synthesized, e.g. likewise according to Scheme 5, by hydrogenating the corresponding aldehyde VIII and subsequently etherifying with the corresponding alcohol.

Scheme 5

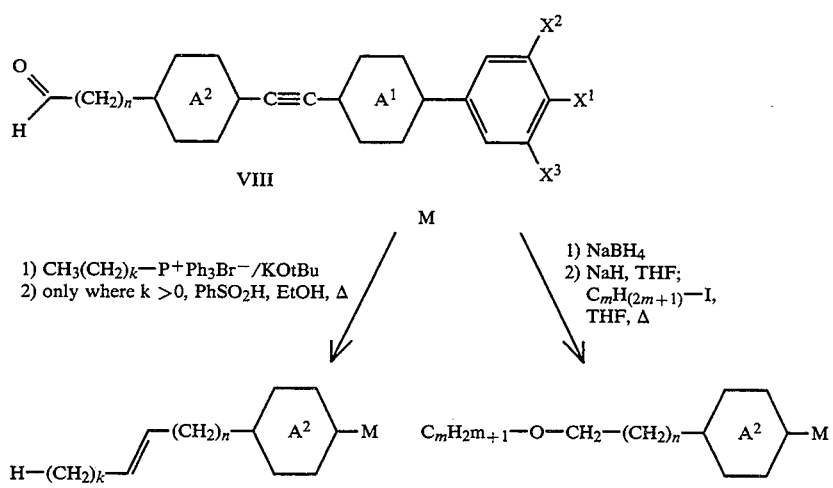

The symbols R, $R^1$, $A^1$, $X^1$, $X^2$, $X^3$ and $X^4$ in Schemes 1 to 5 have the meaning given above.

The compounds of formula I can be used in the form of mixtures with one another and/or with other liquid crystal components. Suitable liquid crystal components will be known in large numbers by a person skilled in the art, e.g. from D. Demus et al., Flüssige Kristalle in Tabellen, VEB Deutscher Verlag für Grundstoffindustrie, Leipzig, volumes I and II, and, moreover, many of them are commercially available.

The invention is accordingly also concerned with liquid crystalline mixtures having at least two components, wherein at least one component is a compound of formula I.

Having regard to the good solubility of the compounds of formula I in other liquid crystal materials and having regard to their good miscibility with one another, the content of compounds of formula I in the mixtures in accordance with the invention can be relatively high and can be, for example, 1–70 wt. %. In general, a content of about 3–40 wt. %, especially of about 5–30 wt. %, of compounds of formula I is preferred.

The mixtures in accordance with the invention preferably contain, in addition to one or more compounds of formula I, one or more compounds from the group of compounds of the general formulas:

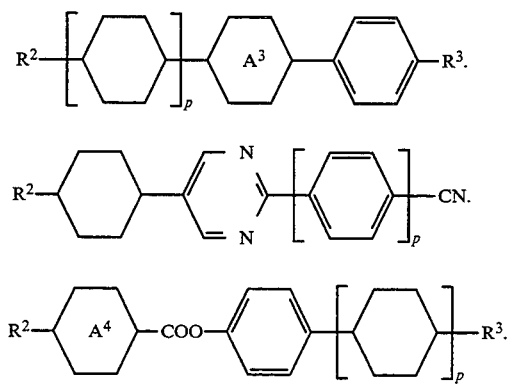

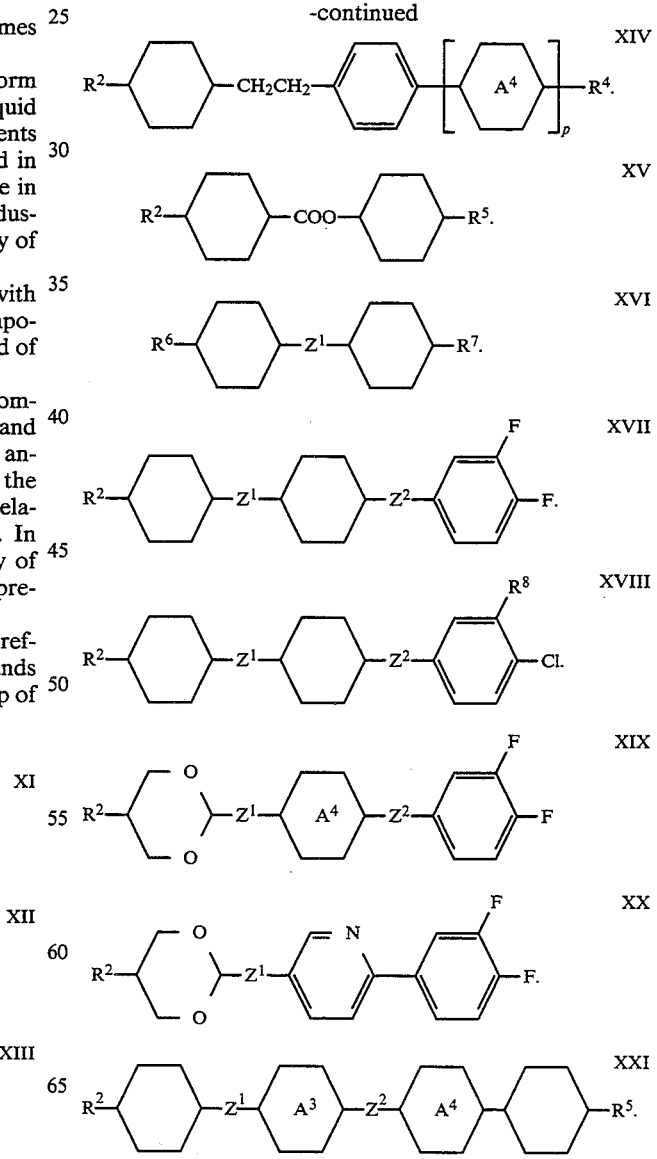

-continued

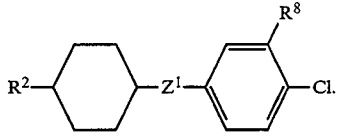 XXII

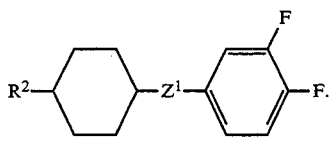 XXIII

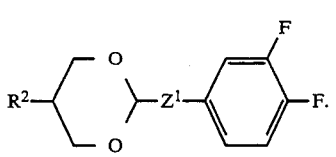 XXIV

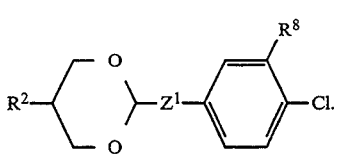 XXV

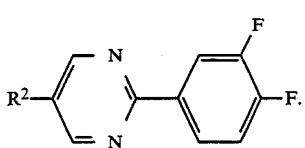 XXVI

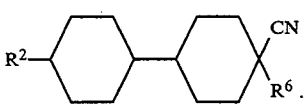 XXVII

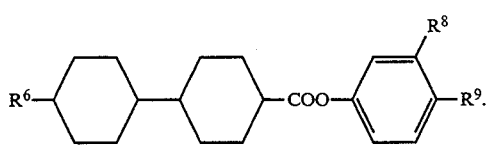 XXVIII

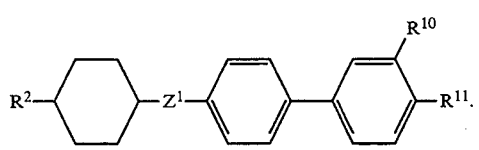 XXIX wherein
$R^2$, $R^5$ are each independently alkyl, alkoxyalkyl, 3E-alkenyl, 4-alkenyl or on saturated rings also 1E-alkenyl;
p is 0 or 1;
ring $A^3$ is 1,4-phenylene, pyridine-2,5-diyl, pyrimidine-2,5-diyl, trans-1,4-cyclohexylene or trans-1,3-dioxane-2,5-diyl;
$R^3$ is cyano, isothiocyanato, fluorine, alkyl, 3E-alkenyl, 4-alkenyl, alkoxy, 2E-alkenyloxy, 3-alkenyloxy or 1-alkynyl;
ring $A^4$ is 1,4-phenylene or trans-1,4-cyclohexylene;
$R^4$ is alkyl, 3E-alkenyl, 4-alkenyl or on trans-1,4-cyclohexylene also 1E-alkenyl or on 1,4-phenylene also cyano, isothiocyanato, alkoxy, 2E-alkenyloxy or 3-alkenyloxy;
$R^6$ is alkyl, 1E-alkenyl, 3E-alkenyl or 4-alkenyl;

$R^7$ is cyano, alkyl, 1E-alkenyl, 3E-alkenyl, 4-alkenyl, alkoxy, 2E-alkenyloxy, 3-alkenyloxy, alkoxymethyl or (2E-alkenyl)alkoxymethyl;
$Z^1$, $Z^2$ each independently are a single covalent bond or $-CH_2CH_2-$, with two aromatic rings always being linked by a single covalent bond;
$R^8$ is hydrogen, fluorine or chlorine;
$R^9$ is cyano, fluorine or chlorine;
$R^{10}$ is hydrogen or fluorine; and
$R^{11}$ is fluorine or chlorine.

The aforementioned term "aromatic rings" means in this connection rings such as, for example, 1,4-phenylene, pyridine-2,5-diyl or pyrimidine-2,5-diyl. The term "saturated rings" means trans-1,4-cyclohexylene or 1,3-dioxane-2,5-diyl.

Residues $R^2$ to $R^7$ each preferably have 1 to 12 carbon atoms, particularly 1 to 7 carbon atoms. Straight-chain residues are generally preferred. The term "alkyl" in this connection preferably means straight-chain residues with 1 to 12 carbon atoms, especially with 1 to 7 carbon atoms such as, for example, methyl, ethyl, propyl, butyl, pentyl, hexyl or heptyl.

The term "alkyloxyalkyl" preferably means in this connection straight-chain residues such as, for example, methoxymethyl, ethoxymethyl, propyloxymethyl, butyloxymethyl and the like.

The term "alkyloxy" preferably means in this connection straight-chain residues such as, for example, methoxy, ethoxy, propyloxy, butyloxy, pentyloxy, hexyloxy, heptyloxy and the like.

The term "1E-alkenyl" preferably means in this connection straight-chain alkenyl residues in which the double bond is situated in the 1-position, such as, for example, vinyl, 1E-propenyl, 1E-butenyl, 1E-pentenyl, 1E-hexenyl, 1E-heptenyl and the like.

The term "3E-alkenyl" preferably means in this connection straight-chain alkenyl residues in which the double bond is situated in the 3-position, such as, for example, 3-butenyl, 3E-pentenyl, 3E-hexenyl, 3E-heptenyl and the like.

The term "4-alkenyl" preferably means in this connection straight-chain alkenyl residues in which the double bond is situated in the 4-position, such as, for example, 4-pentenyl, 4-hexenyl, 4-heptenyl and the like.

The term "2E- or 3Z-alkenyloxy" preferably means in this connection straight-chain alkenyloxy residues in which the double bond is situated in the 2- or 3-position and E or Z indicates the preferred configuration, such as, for example, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy and the like.

The term "1-alkynyl" preferably means in this connection straight-chain alkynyl residues in which the triple bond is situated in the 1-position, such as, for example ethynyl, 1-propynyl, 1-butynyl, 1-pentynyl and the like.

If desired, the mixtures in accordance with the invention can also contain optically active compounds (e.g. optically active 4'-alkyl- or 4'-alkoxy-4-biphenylcarbonitriles) and/or dichroic coloring substances (e.g. azo, azoxy or anthraquinone coloring substances). The content of such compounds is determined by the solubility, the desired pitch, color, extinction and the like. In general, the content of optically active compounds and dichroic coloring substances is a maximum of in each case about 10 wt. % in the final mixture.

The manufacture of the mixtures in accordance with the invention and the manufacture of the electro-optical devices can be effected in a manner known per se.

The preparation of the compounds of formula I and of liquid crystalline mixtures containing these compounds are illustrated in more detail by the following Examples. C means a crystalline phase, S means a smectic phase, N means a nematic phase and I means the isotropic phase. $V_{10}$ means the voltage for 10% transmission (viewing angle perpendicular to the plate surface). $t_{on}$ and $t_{off}$ mean respectively the switching-on time and the switching-off time and $\Delta n$ means the optical anisotropy. The following Examples are intended to illustrate the properties of the compounds in accordance with the invention in more detail.

EXAMPLE 1

A mixture of 1.506 g of 4-bromo-4'-fluorobiphenyl, 1.127 g of (trans-4-propylcyclohexyl)acetylene, 0.138 g of tetrakis(triphenylphosphine)palladium, 0.052 g of copper(I) bromide and 36 ml of triethylamine was heated to boiling for 4.5 hours. After cooling the reaction mixture was diluted with 100 ml of diethyl ether, washed twice with 40 ml of water each time, dried over sodium sulphate, filtered and evaporated. The crude 4-[(trans-4-propylcyclohexyl)ethynyl]-4'-fluorobiphenyl was purified by chromatography on 12 g of silica gel with hexane/ethyl acetate (vol. 49:1) and two-fold recrystallization from hexane; m.p. (C-N) 110.6° C., cl.p. (N-I) 179° C.

In an analogous manner there can be prepared:

4-[(trans-4-ethylcyclohexyl)ethynyl]-4'-fluorobiphenyl;
4-[(trans-4-butylcyclohexyl)ethynyl]-4'-fluorobiphenyl, m.p. (C-S$_A$) 88.7° C., S$_A$-N 94.1° C., cl.p. (N-I) 171° C.;
4-[(trans-4-pentylcyclohexyl)ethynyl]-4'-fluorobiphenyl;
4-[(trans-4-hexylcyclohexyl)ethynyl]-4'-fluorobiphenyl;
4-[(trans-4-heptylcyclohexyl)ethynyl]-4'-fluorobiphenyl;
4-[(trans-4-propylcyclohexyl)ethynyl]-3',4'-dibromobiphenyl, m.p. (C-N) 80.3° C., cl.p. (N-I) 132.5° C.;
b      4-[trans-4-butylcyclohexyl)ethynyl]-3',4'-difluorobiphenyl, m.p. (C-N) 65.8° C., S$_A$-N 47.4° C., Cl.p. (N-I) 127° C.;
4-[(trans-4-pentylcyclohexyl)ethynyl]-3',4'-difluorobiphenyl;
4-[(trans-4-propylcyclohexyl)ethynyl]-4'-chlorobiphenyl, m.p. (C-N) 168.7° C., cl.p. (N-I) 208° C.;
4-[(trans-4-butylcyclohexyl)ethynyl]-4'-chlorobiphenyl, m.p. (C-S$_A$) 138.7° C., S$_A$-N 156.7° C., cl.p. (N-I) 200° C.;
4-[(trans-4-pentylcyclohexyl)ethynyl]-4'-chlorobiphenyl;
4-[(trans-4-propylcyclohexyl)ethynyl]-4'-chloro-3'-fluorobiphenyl, m.p. (C-N) 124.4° C., cl.p. (N-I) 159.5° C.;
4-[(trans-4-butylcyclohexyl)ethynyl]-4'-chloro-3'-fluorobiphenyl, m.p. (C-S$_A$) 88.5° C., S$_A$-N 95.6° C., cl.p. (N-I) 154° C.;
4-[(trans-4-pentylcyclohexyl)ethynyl]-4'-chloro-3'-fluorobiphenyl;
4-[(trans-4-propylcyclohexyl)ethynyl]-4'-bromobiphenyl;
4-[(trans-4-butylcyclohexyl)ethynyl]-4'-bromobiphenyl;
4-[(trans-4-propylcyclohexyl)ethynyl]-4'-trifluoromethoxybiphenyl;
4-[(trans-4-butylcyclohexyl)ethynyl]-4'-trifluoromethoxybiphenyl;
4-[(trans-4-propylcyclohexyl)ethynyl]-4'-difluoromethoxybiphenyl;
4-[(trans-4-butylcyclohexyl)ethynyl]-4'-difluoromethoxybiphenyl;
4-[(trans-4-propylcyclohexyl)ethynyl]-4'-difluoromethoxy-3'-fluorobiphenyl;
4-[(trans-4-butylcyclohexyl)ethynyl]-4'-difluoromethoxy-3'-fluorobiphenyl;
4-[(trans-4-butylcyclohexyl)ethynyl]-3',4',5'-trifluorobiphenyl;
4-[(trans-4-propylcyclohexyl)ethynyl]-4'-(difluoromethoxy)-3',5'-difluorobiphenyl, m.p. (C-N) 62.2° C., cl.p. (N-I) 110° C.;
4-[(trans-4-butylcyclohexyl)ethynyl]-3',5'-difluoro-4'-chlorobiphenyl;
4-(1-butynyl)-4'-fluorobiphenyl;
4-(1-pentynyl)-4'-fluorobiphenyl;
4-(1-hexynyl)-4'-fluorobiphenyl, cl.p. (S-I) 73.7° C.;
4-(1-heptynyl)-4'-fluorobiphenyl;
4-(1-pentynyl)-3',4'-difluorobiphenyl;
4-(1-hexynyl)-3',4'-difluorobiphenyl, m.p. (C-S) 18.8° C., cl.p. (S-I) 22.2° C.;
4-(1-heptynyl)-3',4'-difluorobiphenyl, m.p. (C-I) 20.6° C., cl.p. (S-I) 2° C.;
4-(1-butynyl)-4'-chlorobiphenyl;
4-(1-pentynyl)-4'-chlorobiphenyl;
4-(1-hexynyl)-4'-chlorobiphenyl;
4-(1-heptynyl)-4'-chlorobiphenyl;
4-(1-butynyl)-4'-chloro-3'-fluorobiphenyl;
4-(1-pentynyl)-4'-chloro-3'-fluorobiphenyl;
4-(1-hexynyl)-4'-chloro-3'-fluorobiphenyl;
4-(1-heptynyl)-4'-chloro-3'-fluorobiphenyl;
4-(1-hexynyl)-4'-(trifluoromethoxy)biphenyl;
4-(1-hexynyl)-4'-(difluoromethoxy)biphenyl;
4-(1-hexynyl)-4'-(difluoromethoxy)-3'-fluorobiphenyl;
4-(1-pentynyl)-4'-(difluoromethoxy)-3',5'-difluorophenyl, m.p. (C-I) 19.6° C.;
4-(1-hexynyl)-4'-(difluoromethoxy)-3',5'-difluorophenyl, m.p. (C-I) 34.4° C.;
4-(1-heptynyl)-4'-(difluoromethoxy)3',5'-difluorophenyl, m.p. (C-I) 6.3° C.;
4-(1-hexynyl)-4'-(trifluoromethyl)-3'-fluorobiphenyl;
5-[(trans-4-ethylcyclohexyl)ethynyl]-2-(4-fluorophenyl)pyridine;
5-[(trans-4-propylcyclohexyl)ethynyl]-2-(4-fluorophenyl)pyridine, m.p. (C-N) 73.7° C., S$_A$-N 72.0° C., cl.p. (N-I) 178° C.;
5-[(trans-4-butylcyclohexyl)ethynyl]-2-(4-fluorophenyl)pyridine, m.p. (C-S$_A$) 66.0° C., S$_A$-N 87.5° C., cl.p. (N-I) 170° C.;
5-[(trans-4-pentylcyclohexyl)ethynyl]-2-(4-fluorophenyl)pyridine;
5-[(trans-4-hexylcyclohexyl)ethynyl]-2-(4-fluorophenyl)pyridine;
5-[(trans-4-heptylcyclohexyl)ethynyl]-2-(4-fluorophenyl)pyridine;
5-[(trans-4-propylcyclohexyl)ethynyl]-2-(3,4-difluorophenyl)pyridine, m.p. (C-N) 67.3° C., S$_A$-N 47.2° C., cl.p. (N-I) 137.5° C.;
5-[(trans-4-butylcyclohexyl)ethynyl]-2-(3,4-difluorophenyl)pyridine, m.p. (C-N) 76.2° C., S$_A$-N 55.0C., cl.p. (N-I) 133° C.;
5-[(trans-4-pentylcyclohexyl)ethynyl]-2-(3,4-difluorophenyl)pyridine;

5-[(trans-4-ethylcyclohexyl)ethynyl]-2-(4-chlorophenyl)pyridine;
5-[(trans-4-propylcyclohexyl)ethynyl]-2-(4-chlorophenyl)pyridine, m.p. (C-S$_A$) 118.0° C., S$_A$-N 143.0° C., cI.p. (N-I) 208° C.;
5-[(trans-4-butylcyclohexyl)ethynyl]-2-(4-chlorophenyl)pyridine, m.p. (C-S$_A$) 90.3° C., S$_A$-N 151.8° C., cI.p. (N-I) 202° C.;
5-[(trans-4-pentylcyclohexyl)ethynyl]-2-(4-chlorophenyl)pyridine;
5-[(trans-4-propylcyclohexyl)ethynyl]-2-(4-chloro-3-fluorophenyl)pyridine, m.p. (C-S$_A$) 86.6° C., S$_A$-N 94.3° C., cI.p. (N-I) 165° C.;
5-[(trans-4-butylcyclohexyl)ethynyl]-2-(4-chloro-3-fluorophenyl)pyridine, m.p. (C-S$_A$) 66.1° C., S$_A$-N 101.5° C., cI.p. (N-I) 160° C.;
5-[(trans-4-pentylcyclohexyl)ethynyl]-2-(4-chloro-3-fluorophenyl)pyridine;
5-[(trans-4-butylcyclohexyl)ethynyl]-2-(4-bromophenyl)pyridine;
5-[(trans-4-butylcyclohexyl)ethynyl]-2-[(4-(trifluoromethoxy)phenyl]pyridine;
5-[(trans-4-butylcyclohexyl)ethynyl]-2-[(4-(difluoromethoxy)phenyl]pyridine;
5-[(trans-4-butylcyclohexyl)ethynyl]-2-[(4-(trifluoromethyl)phenyl]pyridine;
5-[(trans-4-propylcyclohexyl)ethynyl]-2-(3,4,5-fluorophenyl)pyridine;
5-[(trans-4-butylcyclohexyl)ethynyl]-2-(4-chloro-3,5-difluorophenyl)pyridine;
5-(1-butynyl)-2-(4-fluorophenyl)pyridine;
5-(1-pentynyl)-2-(4-fluorophenyl)pyridine, m.p. (C-I) 58.3° C., cI.p. (S$_A$-I) 48.8° C.;
5-(1-hexynyl)-2-(4-fluorophenyl)pyridine, m.p. (C-S$_A$) 20.7° C., cI.p. (S$_A$-I) 37.0° C.;
5-(1-heptynyl)-2-(4-fluorophenyl)pyridine, m.p. (C-I) 25.2° C., cI.p. (S$_A$-I) 23.9° C.;
5-(1-pentynyl)-2-(3,4-difluorophenyl)pyridine;
5-(1-hexynyl)-2-(3,4-difluorophenyl)pyridine, m.p. (C-I) 50.4° C., cI.p. (S$_A$-I) 25° C.;
5-(1-heptynyl)-2-(3,4-difluorophenyl)pyridine;
5-(1-pentynyl)-2-(4-chlorophenyl)pyridine;
5-(1-hexynyl)-2-(4-chlorophenyl)pyridine, m.p. (C-S$_A$) 26° C., cI.p. (S$_A$-I) 87.5° C.;
5-(1-heptynyl)-2-(4-chlorophenyl)pyridine;
5-(1-pentynyl)-2-(4-chloro-3-fluorophenyl)pyridine, m.p. (C-I) 63.30° C., cI.p. (S$_A$-I) 61.9° C.;
5-(1-hexynyl)-2-(4-chloro-3-fluorophenyl)pyridine;
5-(1-heptynyl)-2-(4-chloro-3-fluorophenyl)pyridine;
5-(1-hexynyl)-2-(4-bromophenyl)pyridine;
5-(1-hexynyl)-2-[4-(trifluoromethoxy)phenyl]pyridine;
5-(1-hexynyl)-2-[4-(difluoromethoxy)phenyl]pyridine;
5-(1-hexynyl)-2-[4-(difluoromethoxy)-3-fluorophenyl]pyridine;
5-(1-hexynyl)-2-[4-(trifluoromethyl)phenyl]pyridine;
5-[(trans-4-ethylcyclohexyl)ethynyl]-2-(4-fluorophenyl)pyrimidine;
5-[(trans-4-propylcyclohexyl)ethynyl]-2-(4-fluorophenyl)pyrimidine, m.p. (C-N) 117.3° C., S$_A$-N 95.8° C., cI.p. (N-I) 180.5° C.;
5-[(trans-4-butylcyclohexyl)ethynyl]-2-(4-fluorophenyl)pyrimidine, m.p. (C-S$_A$) 104.9° C., S$_A$-N 109.5° C., cI.p. (N-I) 175° C.;
5-[(trans-4-pentylcyclohexyl)ethynyl]-2-(4-fluorophenyl)pyrimidine;
5-[(trans-4-hexylcyclohexyl)ethynyl]-2-(4-fluorophenyl)pyrimidine;
5-[(trans-4-heptylcyclohexyl)ethynyl]-2-(4-fluorophenyl)pyrimidine;
5-[(trans-4-propylcyclohexyl)ethynyl]-2-(3,4-difluorophenyl)pyrimidine, m.p. (C-N) 109.3° C., cI.p. (N-I) 152° C.;
5-[(trans-4-butylcyclohexyl)ethynyl]-2-(3,4-difluorophenyl)pyrimidine, m.p. (C-N) 99.6° C., S$_A$-N 97.3° C., cI.p. (N-I) 147.5° C.;
5-[(trans-4-pentylcyclohexyl)ethynyl]-2-(3,4-difluorophenyl)pyrimidine;
5-[(trans-4-ethylcyclohexyl)ethynyl]-2-(4-chlorophenyl)pyrimidine;
5-[(trans-4-propylcyclohexyl)ethynyl]-2-(4-chlorophenyl)pyrimidine, m.p. (C-S$_A$) 131.1° C., S$_A$-N 148.0° C., cI.p. (N-I) 208° C.;
5-[(trans-4-butylcyclohexyl)ethynyl]-2-(4-chlorophenyl)pyrimidine, m.p. (C-S$_A$) 99.5° C., S$_A$-N 156° C., cI.p. (N-I) 202.5° C.;
5-[(trans-4-pentylcyclohexyl)ethynyl]-2-(4-chlorophenyl)pyrimidine;
5-[(trans-4-propylcyclohexyl)ethynyl]-2-(4-chloro-3-fluorophenyl)pyrimidine, m.p. (C-S$_A$) 96.1° C., S$_A$-N 120.6° C., cI.p. (N-I) 171.5° C.;
5-[(trans-4-butylcyclohexyl)ethynyl]-2-(4-chloro-3-fluorophenyl)pyrimidine, m.p. (C-S$_A$) 111.3° C., S$_A$-N 129.3° C., cI.p. (N-I) 171° C.;
5-[(trans-4-pentylcyclohexyl)ethynyl]-2-(4-chloro-3-fluorophenyl)pyrimidine;
5-(1-pentynyl)-2-(4-fluorophenyl)pyrimidine;
5-(1-hexynyl)-2-(4-fluorophenyl)pyrimidine, m.p. (C-I) 69.5° C., cI.p. (S$_A$-I) 41.0° C.;
5-(1-heptynyl)-2-(4-fluorophenyl)pyrimidine;
5-(1-butynyl)-2-(3,4-difluorophenyl)pyrimidine;
5-(1-pentynyl)-2-(3,4-difluorophenyl)pyrimidine, m.p. (C-I) 73.1° C., cI.p. (S$_A$-I) 62.6° C.;
5-(1-hexynyl)-2-(3,4-difluorophenyl)pyrimidine, m.p. (C-S$_A$) 55.5° C., cI.p. (S$_A$-I) 61.5° C.;
5-(1-heptynyl)-2-(3,4-difluorophenyl)pyrimidine;
5-(1-octynyl)-2-(3,4-difluorophenyl)pyrimidine;
5-(1-nonynyl)-2-(3,4-difluorophenyl)pyrimidine;
5-(1-pentynyl)-2-(4-chlorophenyl)pyrimidine, m.p. (C-I) 121.20° C.;
5-(1-hexynyl)-2-(4-chlorophenyl)pyrimidine, m.p. (C-S$_A$) 76.3° C., cI.p. (S$_A$-I) 82.6° C.;
5-(1-heptynyl)-2-(4-chlorophenyl)pyrimidine, m.p. (C-S$_A$) 79.8° C., cI.p. (S$_A$-I) 80.8° C.;
5-(1-pentynyl)-2-(4-chloro-3-fluorophenyl)pyrimidine, m.p. (C-I) 101.4° C., cI.p. (S$_A$-I) 88.7° C.;
5-(1-hexynyl)-2-(4-chloro-3-fluorophenyl)pyrimidine, m.p. (C-I) 81.1° C., cI.p. (S$_A$-I) 78.4° C.;
5-(1-heptynyl)-2-(4-chloro-3-fluorophenyl)pyrimidine, m.p. (C-S$_A$) 72.1° C., cI.p. (S$_A$-I) 72.6° C.;
5-(1-octynyl)-2-(4-chloro-3-fluorophenyl)pyrimidine;
5-(1-hexynyl)-2-(4-bromophenyl)pyrimidine;
5-(1-hexynyl)-2-(4-bromo-3-fluorophenyl)pyrimidine;
5-(1-hexynyl)-2-[4-(trifluoromethoxy)phenyl]pyrimidine;
5-(1-hexynyl)-2-[4-(difluoromethoxy)phenyl]pyrimidine;
5-(1-hexynyl)-2-[4-(difluoromethoxy)-3-fluorophenyl]pyrimidine;
5-(1-hexynyl)-2-[4-(trifluoromethyl)phenyl]pyrimidine;
5-(1-hexynyl)-2-[4-(trifluoromethyl)-3-fluorophenyl]pyrimidine.

EXAMPLE 2 a) A mixture of 2.00 g of crude 5-bromo-2-(3,4-difluorophenyl)pyridine (GC purity 81%), 1.12 ml of 3,3-diethoxy-1-propine, 0.138 g of tetrakis(triphenylphosphine)palladium, 0.052 g of copper(I) bromide and 36 ml of triethylamine was heated to boiling for 2 hours. After cooling the reaction mixture was diluted with 100 ml of diethyl ether, washed twice with 40 ml of water each time, dried over sodium sulphate, filtered, the filtrate was boiled briefly with active charcoal, filtered and concentrated. The crude 5-(3,3-diethoxy-1-propynyl)-2-(3,4-difluorophenyl)pyridine, (2.58 g; GC purity 72%), obtained as a brown-black oil, was used directly in the next step.

b) A mixture of 0.86 g of crude 5-(3,3-diethoxy-1-propynyl)-2-(3,4-difluorophenyl)pyridine, 0.60 g of 2-propyl-1,3-propanediol, 50 ml of benzene, 24 drops of water and 12. drops of 10% sulphuric acid (v/v) was stirred at 73° C. for 0.5 hour, then heated to boiling for 1 hour, with moist benzene being distilled off and being replaced by fresh benzene. The reaction mixture was washed with 30 ml of saturated sodium hydrogen carbonate solution and 30 ml of water, dried over sodium sulphate, filtered and concentrated. The crude 5-[(trans-5-propyl-1,3-dioxan-2-yl)ethynyl]-2-(3,4-difluorophenyl)pyridine was purified by chromatography on 16 g of silica gel with hexane/ethyl acetate (vol. 9:1) and two-fold recrsytallization from ethyl acetate; m.p. (C-N) 12.4.7° C., cl.p. (N-I) 128.4° C.

In an analogous manner there can be prepared:

5-[(trans-5-propyl-1,3-dioxan-2-yl)ethynyl]-2-(4-fluorophenyl)pyridine;
5-[(trans-5-butyl-1,3-dioxan-2-yl)ethynyl]-2-(4-fluorophenyl)pyridine;
5-[(trans-5-pentyl-1,3-dioxan-2-yl)ethynyl]-2-(4-fluorophenyl)pyridine;
5-[(trans-5-(1E-propenyl)-1,3-dioxan-2-yl)ethynyl]-2-(4-fluorophenyl)pyridine;
5-[(trans-5-(1E-butenyl)-1,3-dioxan-2-yl)ethynyl]-2-(4-fluorophenyl)pyridine;
5-[(trans-5-(1E-pentenyl)-1,3-dioxan-2-yl)ethynyl]-2-(4-fluorophenyl)pyridine;
5-[(trans-5-(3-butenyl)-1,3-dioxan-2-yl)ethynyl]-2-(4-fluorophenyl)pyridine;
5-[(trans-5-(4-pentenyl)-1,3-dioxan-2-yl)ethynyl]-2-(4-fluorophenyl)pyridine;
5-[(trans-5-butyl-1,3-dioxan-2-yl)ethynyl]-2-(3,4-difluorophenyl)pyridine;
5-[(trans-5-pentyl-1,3-dioxan-2-yl)ethynyl]-2-(3,4-difluorophenyl)pyridine;
5-[(trans-5-(1E-propenyl)-1,3-dioxan-2-yl)ethynyl]-2-(3,4-difluorophenyl)pyridine, m.p. (C-N) 155.5° C., cl.p. (N-I) 173° C.;
5-[(trans-5-(1E-butenyl)-1,3-dioxan-2-yl)ethynyl]-2-(3,4-difluorophenyl)pyridine;
5-[(trans-5-(1E-pentenyl)-1,3-dioxan-2-yl)ethynyl]-2-(3,4-difluorophenyl)pyridine;
5-[(trans-5-(3-butenyl-1,3-dioxan-2-yl)ethynyl]-2-(3,4-difluorophenyl)pyridine, m.p. (C-N) 109.2° C., S$_A$-N 91.5° C., cl.p. (N-I) 118° C.;
5-[(trans-5-(4-pentenyl)-1,3-dioxan-2-yl)ethynyl]-2-(3,4-difluorophenyl)pyridine;
5-[(trans-5-(4-propyl-1,3-dioxan-2-yl)ethynyl]-2-(4-chlorophenyl)pyridine;
5-[(trans-5-(4-butyl-1,3-dioxan-2-yl)ethynyl]-2-(4-chlorophenyl)pyridine;
5-[(trans-5-(4-pentyl-1,3-dioxan-2-yl)ethynyl]-2-(4-chlorophenyl)pyridine;
5-[(trans-5-(1E-propenyl)-1,3-dioxan-2-yl)ethynyl]-2-(4-chlorophenyl)pyridine;
5-[(trans-5-(1E-butenyl)-1,3-dioxan-2-yl)ethynyl]-2-(4-chlorophenyl)pyridine;
5-[(trans-5-(1E-pentenyl)-1,3-dioxan-2-yl)ethynyl]-2-(4-chlorophenyl)pyridine;
5-[(trans-5-(3-butenyl)-1,3-dioxan-2-yl)ethynyl]-2-(4-chlorophenyl)pyridine;
5-[(trans-5-(4-pentenyl)-1,3-dioxan-2-yl)ethynyl]-2-(4-chlorophenyl)pyridine;
5-[(trans-5-propyl-1,3-dioxan-2-yl)ethynyl]-2-(4-chloro-3-fluorophenyl)pyridine;
5-[(trans-5-butyl-1,3-dioxan-2-yl)ethynyl]-2-(4-chloro-3-fluorophenyl)pyridine;
5-[(trans-5-pentyl-1,3-dioxan-2-yl)ethynyl]-2-(4-chloro-3-fluorophenyl)pyridine;
5-[(trans-5-(1E-propenyl)-1,3-dioxan-2-yl)ethynyl]-2-(4-chloro-3-fluorophenyl)pyridine;
5-[(trans-5-(1E-butenyl)-1,3-dioxan-2-yl)ethynyl]-2-(4-chloro-3-fluorophenyl)pyridine;
5-[(trans-5-(1E-pentenyl)-1,3-dioxan-2-yl)ethynyl]-2-(4-chloro-3-fluorophenyl)pyridine;
5-[(trans-5-(3-butenyl)-1,3-dioxan-2-yl)ethynyl]-2-(4-chloro-3-fluorophenyl)pyridine;
5-[(trans-5-(4-pentenyl)-1,3-dioxan-2-yl)ethynyl]-2-(4-chloro-3-fluorophenyl)pyridine;
5-[(trans-5-propyl-1,3-dioxan-2-yl)ethynyl]-2-[4-(trifluoromethoxy)phenyl)pyridine;
5-[(trans-5-butyl-1,3-dioxan-2-yl)ethynyl]-2-[4-(trifluoromethoxy)phenyl)pyridine;
5-[(trans-5-pentyl-1,3-dioxan-2-yl)ethynyl]-2-[4-(trifluoromethoxy)phenyl)pyridine;
5-[(trans-5-(1E-propenyl)-1,3-dioxan-2-yl)ethynyl]-2-[4-(trifluoromethoxy)phenyl)pyridine;
5-[(trans-5-propyl-1,3-dioxan-2-yl)ethynyl]-2-[4-(difluoromethoxy)phenyl]pyridine;
5-[(trans-5-butyl-1,3-dioxan-2-yl)ethynyl]-2-[4-(difluoromethoxy)phenyl]pyridine;
5-[(trans-5-(1E-propenyl)-1,3-dioxan-2-yl)ethynyl]-2-[4-(difluoromethoxy)phenyl]pyridine;
5-[(trans-5-(1E-butenyl-1,3-dioxan-2-yl)ethynyl]-2-[4-(difluoromethoxy)phenyl]pyridine;
-[(trans-5-butyl-1,3-dioxan-2-yl)ethynyl]-2-[4-(trifluoromethyl)phenyl]pyridine;
5-[(trans-5-propyl-1,3-dioxan-2-yl)ethynyl]-2-(4-fluorophenyl)pyrimidine;
5-[(trans-5-butyl-1,3-dioxan-2-yl)ethynyl]-2-(4-fluorophenyl)pyrimidine;
5-[(trans-5-pentyl-1,3-dioxan-2-yl)ethynyl]-2-(4-fluorophenyl)pyrimidine;
5-[(trans-5-(1E-propenyl)-1,3-dioxan-2-yl)ethynyl]-2-(4-fluorophenyl)pyrimidine;
5-[(trans-5-(1E-butenyl)-1,3-dioxan-2-yl)ethynyl]-2-(4-fluorophenyl)pyrimidine;
5-[(trans-5-(3-butenyl)-1,3-dioxan-2-yl)ethynyl]-2-(4-fluorophenyl)pyrimidine;
5-[(trans-5-(4-pentenyl)-1,3-dioxan-2-yl)ethynyl]-2-(4-fluorophenyl)pyrimidine;
5-[(trans-5-propyl-1,3-dioxan-2-yl)ethynyl]-2-(3,4-difluorophenyl)pyrimidine, m.p. (C-N) 147.1° C., S$_A$-N 117.0° C., cl.p. (N-I) 156° C.;
5-[(trans-5-butyl-1,3-dioxan-2-yl)ethynyl]-2-(3,4-difluorophenyl)pyrimidine;
5-[(trans-5-pentyl-1,3-dioxan-2-yl)ethynyl]-2-(3,4-difluorophenyl)pyrimidine;
5-[(trans-5-(1E-propenyl)-1,3-dioxan-2-yl)ethynyl]-2-(3,4-difluorophenyl)pyrimidine, m.p. (C-N) 171.50° C., cl.p. (N-I) 201° C.;
5-[(trans-5-(1E-butenyl)-1,3-dioxan-2-yl)ethynyl]-2-(3,4-difluorophenyl)pyrimidine;

5-[(trans-5-(3-butenyl)-1,3-dioxan-2-yl)ethynyl]-2-(3,4-difluorophenyl)pyrimidine, m.p. (C-N) 136° C., S$_A$-N 124.4° C., cl.p. (N-I) 144° C.;

5-[(trans-5-(4-pentenyl)-1,3-dioxan-2-yl)ethynyl]-2-(3,4-difluorophenyl)pyrimidine;

5-[(trans-5-propyl-1,3-dioxan-2-yl)ethynyl]-2-(4-chlorophenyl)pyrimidine;

5-[(trans-5-butyl-1,3-dioxan-2-yl)ethynyl]-2-(4-chlorophenyl)pyrimidine;

5-[(trans-5-(1E-propenyl)-1,3-dioxan-2-yl)ethynyl]-2-(4-chlorophenyl)pyrimidine;

5-[(trans-5-(3-butenyl)-1,3-dioxan-2-yl)ethynyl]-2-(4-chlorophenyl)pyrimidine;

5-[(trans-5-(4-pentenyl)-1,3-dioxan-2-yl)ethynyl]-2-(4-chlorophenyl)pyrimidine;

5-[(trans-5-propyl-1,3-dioxan-2-yl)ethynyl]-2-(4-chloro-3-fluorophenyl)pyrimidine;

5-[(trans-5-butyl-1,3-dioxan-2-yl)ethynyl]-2-(4-chloro-3-fluorophenyl)pyrimidine;

5-[(trans-5-pentyl-1,3-dioxan-2-yl)ethynyl]-2-(4-chloro-3-fluorophenyl)pyrimidine;

5-[(trans-5-(1E-propenyl)-1,3-dioxan-2-yl)ethynyl]-2-(4-chloro-3-fluorophenyl)pyrimidine;

5-[(trans-5-(1E-butenyl)-1,3-dioxan-2-yl)ethynyl]-2-(4-chloro-3-fluorophenyl)pyrimidine;

5-[(trans-5-(3-butenyl)-1,3-dioxan-2-yl)ethynyl]-2-(4-chloro-3-fluorophenyl)pyrimidine;

5-[(trans-5-(4-pentenyl)-1,3-dioxan-2-yl)ethynyl]-2-(4-chloro-3-fluorophenyl)pyrimidine;

5-[(trans-5-propyl-1,3-dioxan-2-yl)ethynyl]-2-[4-(difluoromethoxy)phenyl)pyrimidine;

-[(trans-5-butyl-1,3-dioxan-2-yl)ethynyl]-2-[4-(difluoromethoxy)phenyl)pyrimidine;

5-[(trans-5-(1E-propenyl)-1,3-dioxan-2-yl)ethynyl]-2-[4-(difluoromethoxy)phenyl)pyrimidine;

4-[(trans-5-propyl-1,3-dioxan-2-yl)ethynyl]-4'-fluorobiphenyl;

4-[(trans-5-butyl-1,3-dioxan-2-yl)ethynyl]-4'-fluorobiphenyl;

4-[(trans-5-pentyl-1,3-dioxan-2-yl)ethynyl]-4'-fluorobiphenyl;

4-[(trans-5-(1E-propenyl)-1,3-dioxan-2-yl)ethynyl]-4'-fluorobiphenyl;

4-[(trans-5-(1E-butenyl)-1,3-dioxan-2-yl)ethynyl]-4'-fluorobiphenyl;

4-[(trans-5-(1E-pentenyl)-1,3-dioxan-2-yl)ethynyl]-4'-fluorobiphenyl;

4-[(trans-5-(3-butenyl)-1,3-dioxan-2-yl)ethynyl]-4'-fluorobiphenyl;

4-[(trans-5-(4-pentenyl)-1,3-dioxan-2-yl)ethynyl]-4'-fluorobiphenyl;

4-[(trans-5-propyl-1,3-dioxan-2-yl)ethynyl]-3',4'-difluorobiphenyl;

4-[(trans-5-butyl-1,3-dioxan-2-yl)ethynyl]-3',4'-difluorobiphenyl;

4-[(trans-5-pentyl-1,3-dioxan-2-yl)ethynyl]-3',4'-difluorobiphenyl;

4-[(trans-5-(1E-propenyl)-1,3-dioxan-2-yl)ethynyl]-3',4'-difluorobiphenyl, m.p. (C-N) 134.4° C., cl.p. (N-I) 171° C.;

4-[(trans-5-(1E-butenyl)-1,3-dioxan-2-yl)ethynyl]-3',4'-difluorobiphenyl;

4-[(trans-5-(1E-pentenyl)-1,3-dioxan-2-yl)ethynyl]-3',4'-difluorobiphenyl;

4-[(trans-5-(3-butenyl)-1,3-dioxan-2-yl)ethynyl]-3',4'-difluorobiphenyl;

4-[(trans-5-(4-pentenyl)-1,3-dioxan-2-yl)ethynyl]-3',4'-difluorobiphenyl;

4-[(trans-5-propyl-1,3-dioxan-2-yl)ethynyl]-4'-chlorobiphenyl;

4-[(trans-5-butyl-1,3-dioxan-2-yl)ethynyl]-4'-chlorobiphenyl;

4-[(trans-5-pentyl-1,3-dioxan-2-yl)ethynyl]-4'-chlorobiphenyl;

4-[(trans-5-(1E-propenyl)-1,3-dioxan-2-yl)ethynyl]-4'-chlorobiphenyl;

4-[(trans-5-(1E-butenyl)-1,3-dioxan-2-yl)ethynyl]-4'-chlorobiphenyl;

4-[(trans-5-(1E-pentenyl)-1,3-dioxan-2-yl)ethynyl]-4'-chlorobiphenyl;

4-[(trans-5-(3-butenyl)-1,3-dioxan-2-yl)ethynyl]-4'-chlorobiphenyl;

4-[(trans-5-(4-pentenyl)-1,3-dioxan-2-yl)ethynyl]-4'-chlorobiphenyl;

4-[(trans-5-propyl-1,3-dioxan-2-yl)ethynyl]-4'-chloro-3'-fluorobiphenyl;

4-[(trans-5-butyl-1,3-dioxan-2-yl)ethynyl]-4'-chloro-3'-fluorobiphenyl;

4-[(trans-5-pentyl-1,3-dioxan-2-yl)ethynyl]-4'-chloro-3'-fluorobiphenyl;

5-[(trans-5-(1E-propenyl)-1,3-dioxan-2-yl)ethynyl]-4'-chloro-3'-fluorobiphenyl;

4-[(trans-5-(1E-butenyl)-1,3-dioxan-2-yl)ethynyl]-4'-chloro-3'-fluorobiphenyl;

4-[(trans-5-(1E-pentenyl)-1,3-dioxan-2-yl)ethynyl]-4'-chloro-3'-fluorobiphenyl;

4-[(trans-5-(3-butenyl)-1,3-dioxan-2-yl)ethynyl]-4'-chloro-3'-fluorobiphenyl;

4-[(trans-5-(4-pentenyl)-1,3-dioxan-2-yl)ethynyl]-4'-chloro-3'-fluorobiphenyl

4-[(trans-5-propyl-1,3-dioxan-2-yl)ethynyl]-4'-trifluoromethoxy)biphenyl;

4-[(trans-5-(1E-propenyl)-1,3-dioxan-2-yl)ethynyl]-4'-(trifluoromethoxy)biphenyl;

4-[(trans-5-(propyl)-1,3-dioxan-2-yl)ethynyl]-4'-(difluoromethoxy)biphenyl;

4-[(trans-5-(butyl)-1,3-dioxan-2-yl)ethynyl]-4'-(difluoromethoxy)biphenyl;

4-[(trans-5-(1E-propenyl)-1,3-dioxan-2-yl)ethynyl]-4'-(difluoromethoxy)biphenyl;

4-[(trans-5-(3-butenyl)-1,3-dioxan-2-yl)ethynyl]-4'-(difluoromethoxy)biphenyl;

4-[(trans-5-(4-pentenyl)-1,3-dioxan-2-yl)ethynyl]-4'-(difluoromethoxy)biphenyl;

4-[(trans-5-propyl-1,3-dioxan-2-yl)ethynyl]-4'-(trifluoromethyl)biphenyl;

4-[(trans-5-(1E-propenyl)-1,3-dioxan-2-yl)ethynyl]-4'-(trifluoromethyl)biphenyl.

EXAMPLE 3

0.73 g of potassium t-butylate was added to a suspension of 2.3 g of methyltriphenylphosphonium bromide in 25 ml of t-butyl methyl ether in a nitrogen atmosphere and the mixture was stirred at room temperature for 0.5 hour. Then, a solution of 0.8 g of trans-4-[(4'-fluoro-4-biphenylyl)ethynyl]cyclohexanecarboxaldehyde in 25 ml of t-butyl methyl ether was added dropwise at 0° C. and the reaction mixture was stirred at 0° C. for a further 0.5 hour and at room temperature for 2.5 hours, thereafter washed with 50 ml of saturated sodium hydrogen carbonate solution and with 50 ml of saturated sodium chloride solution, dried over sodium sulphate, filtered and concentrated. The residue was chromatographed on silica gel with hexane. The 4-[(trans-4-vinylcyclohexyl)ethynyl]-4'-fluorobiphenyl obtained was purified by recrystallization from hexane; m.p. (C-N) 133.9° C., cl.p. (N-I) 170° C.

The trans-4-[(4'-fluoro-4-biphenylyl)ethynyl]cyclohexanecarboxaldehyde used as the starting material was prepared as follows:

a) A mixture of 1.03 g of 8-ethynyl-1,4-dioxaspiro[4.5]decane, 1.197 g 4-bromo-4'-fluorobiphenyl, 0.11 g of tetrakis(triphenylphosphine)palladium, 0.041 g of copper(I) bromide and 45 ml of triethylamine was heated to boiling for 4.5 hours. After cooling the mixture was diluted with diethyl ether, washed twice with water, dried over sodium sulphate, filtered and concentrated. The crude 8-[(4'-fluoro-4-biphenylyl)ethynyl]-1,4-dioxaspiro[4.5]decane (1.82. g) obtained was purified by chromatography on 35 g of silica gel with hexane/ethyl acetate (vol. 9:1). Yield 1.30 g.

b) A solution of 1.30 g of 8-[(4'-fluoro-4-biphenylyl)ethynyl]-1,4-dioxaspiro[4.5]decane in 30 ml of tetrahydrofuran was stirred with 3.5 ml of 3N hydrochloric acid for 2.4 hours. The reaction mixture was diluted with diethyl ether, washed with saturated sodium hydrogen carbonate solution and with saturated sodium chloride solution, dried over sodium sulphate, filtered and concentrated. 1.11 g of 4-[(4'-fluoro-4-biphenylyl)ethynyl]cyclohexanone were obtained.

c) 0.52 g of potassium t-butylate was added to a suspension of 1.60 g of (methoxymethyl)triphenylphosphonium chloride in 40 ml of t-butyl methyl ether in a nitrogen atmosphere and the orange-red suspension was stirred at room temperature for 0.5 hour. A solution of 1.11 g of 4-[(4'-fluoro-4-biphenylyl)ethynyl]cyclohexanone in 30 ml of tetrahydrofuran was then added dropwise at 5° C. The reaction mixture was stirred at 5° C. for a further 0.5 hour and at room temperature for 2 hours, diluted with diethyl ether, washed with 50 ml of saturated sodium hydrogen carbonate solution and with 50 ml of saturated sodium chloride solution, dried over sodium sulphate, filtered and concentrated. Chromatography of the residue on silica gel with hexane/ethyl acetate (vol. 19:1) yielded 0.95 g of 4'-fluoro-4-[[4-(methoxymethylidene)cyclohexyl]ethynyl]biphenyl.

d) A solution of 0.95 g of 4'-fluoro-4-[[4-(methoxymethylidene)cyclohexyl]ethynyl]biphenyl in 40 ml of toluene was treated with 4 ml of formic acid and stirred at room temperature overnight. The formic acid phase was separated and the toluene phase was washed neutral with water, dried over sodium sulphate, filtered and concentrated. For the ring isomerization, the resulting crude 4-[(4'-fluoro-4-biphenylyl)ethynyl]cyclohexanecarboxaldehyde was dissolved in 35 ml of ethanol, treated with 8.2 ml of 0.1N alcoholic potassium hydroxide solution and stirred at room temperature for 2 hours. The reaction mixture was diluted with diethyl ether, washed with saturated sodium hydrogen carbonate solution and with water, dried over sodium sulphate, filtered and concentrated. 0.80 g of trans-4-[(4'-fluoro-4-biphenylyl)ethynyl]cyclohexanecarboxaldehyde was obtained.

In an analogous manner there can be prepared:

4-[(trans-4-vinylcyclohexyl)ethynyl]-3',4'-difluorobiphenyl;
4-[(trans-4-vinylcyclohexyl)ethynyl]-4'-chlorobiphenyl;
4-[(trans-4-vinylcyclohexyl)ethynyl]-4'-chloro-3'-fluorobiphenyl;
4-[(trans-4-vinylcyclohexyl)ethynyl]-4'-bromobiphenyl;
4-[(trans-4-vinylcyclohexyl)ethynyl]-4'-(trifluoromethoxy)biphenyl;
4-[(trans-4-vinylcyclohexyl)ethynyl]-4'-(difluoromethoxy)-3'-fluorobiphenyl;
4-[(trans-4-vinylcyclohexyl)ethynyl]-4'-(trifluoromethyl)biphenyl;
5-[(trans-4-vinylcyclohexyl)ethynyl]-2-(4-fluorophenyl)pyridine;
5-[(trans-4-vinylcyclohexyl)ethynyl]-2-(3,4-difluorophenyl)pyridine;
5-[(trans-4-vinylcyclohexyl)ethynyl]-2-(4-chlorophenyl)pyridine;
5-[(trans-4-vinylcyclohexyl)ethynyl]-2-(4-chloro-3-fluorophenyl)pyridine;
5-[(trans-4-vinylcyclohexyl)ethynyl]-2-(4-fluorophenyl)pyrimidine;
5-[(trans-4-vinylcyclohexyl)ethynyl]-2-(3,4-difluorophenyl)pyrimidine;
5-[(trans-4-vinylcyclohexyl)ethynyl]-2-(4-chlorophenyl)pyrimidine;
5-[(trans-4-vinylcyclohexyl)ethynyl]-2-(4-chloro-3-fluorophenyl)pyrimidine.

EXAMPLE 4

In analogous manner to Example 3, from 2.4 g of ethyltriphenylphosphonium bromide, 0.73 g of potassium t-butylate and 0.8 g of trans-4-[(4'-fluoro-4-biphenylyl)ethynyl]cyclohexanecarboxaldehyde in t-butyl methyl ether there is obtained, after working-up and chromatography, 0.68 g of crude 4-[trans-4-(1Z-propenylcyclohexyl)ethynyl]-4'-fluorobiphenyl. For the isomerization, this is dissolved in 30 ml of ethanol and treated with 560 mg of benzenesulphinic acid. The mixture is heated to 60° C. overnight and then concentrated. The residue is taken up in diethyl ether and water, the aqueous phase is separated and the organic phase is washed neutral with water, dried over sodium sulphate, filtered and concentrated. Repeated recrystallization of the residue from hexane yields pure 4-[trans-4-(1E-propenylcyclohexyl)ethynyl]-4'-fluorobiphenyl.

In an analogous manner there can be prepared:

4-[[trans-4-(1E-butenyl)cyclohexyl]ethynyl]-4'-fluorobiphenyl;
4-[[trans-4-(1E-pentenyl)cyclohexyl]ethynyl]-4'-fluorobiphenyl;
4-[[trans-4-(1E-propenyl)cyclohexyl]ethynyl]-3',4'-difluorobiphenyl;
4-[[trans-4-(1E-butenyl)cyclohexyl]ethynyl]-3',4'-difluorobiphenyl;
4-[[trans-4-(1E-pentenyl)cyclohexyl]ethynyl]-3',4'-difluorobiphenyl;
4-[[trans-4-(1E-propenyl)cyclohexyl]ethynyl]-4'-chlorobiphenyl;
4-[[trans-4-(1E-butenyl)cyclohexyl]ethynyl]-4'-chlorobiphenyl;
4-[[trans-4-(1E-propenyl)cyclohexyl]ethynyl]-4'-chloro-3'-fluorobiphenyl;
4-[[trans-4-(1E-butenyl)cyclohexyl]ethynyl]-4'-chloro-3'-fluorobiphenyl;
4-[[trans-4-(1E-pentenyl)cyclohexyl]ethynyl]-4'-chloro-3'-fluorobiphenyl;
5-[[trans-4-(1E-propenyl)cyclohexyl]ethynyl]-2-(4-fluorophenyl)pyridine;
5-[[trans-4-(1E-butenyl)cyclohexyl]ethynyl]-2-(4-fluorophenyl)pyridine;
5-[[trans-4-(1E-Pentenyl)cyclohexyl]ethynyl]-2-(4-fluorophenyl)pyridine;
5-[[trans-4-(1E-propenyl)cyclohexyl]ethynyl]-2-(3,4-difluorophenyl)pyridine;

5-[[trans-4-(1E-butenyl)cyclohexyl]ethynyl]-2-(3,4-difluorophenyl)pyridine;
5-[[trans-4-(1E-pentenyl)cyclohexyl]ethynyl]-2-(3,4-difluorophenyl)pyridine;
5-[[trans-4-(1E-propenyl)cyclohexyl]ethynyl]-2-(4-chlorophenyl)pyridine;
5-[[trans-4-(1E-butenyl)cyclohexyl]ethynyl]-2-(4-chlorophenyl)pyridine;
5-[[trans-4-(1E-propenyl)cyclohexyl]ethynyl]-2-(4-chloro-3-fluorophenyl)pyridine;
5-[[trans-4-(1E-butenyl)cyclohexyl]ethynyl]-2-(4-chloro-3-fluorophenyl)pyridine;
5-[[trans-4-(1E-pentenyl)cyclohexyl]ethynyl]-2-(4-chloro-3-fluorophenyl)pyridine;
5-[[trans-4-(1E-propenyl)cyclohexyl]ethynyl]-2-(4-fluorophenyl)pyrimidine;
5-[[trans-4-(1E-butenyl)cyclohexyl]ethynyl]-2-(4-fluorophenyl)pyrimidine;
5-[[trans-4-(1E-propenyl)cyclohexyl]ethynyl]-2-(3,4-difluorophenyl)pyrimidine;
5-[[trans-4-(1E-butenyl)cyclohexyl]ethynyl]-2-(3,4-difluorophenyl)pyrimidine;
5-[[trans-4-(1E-propenyl)cyclohexyl]ethynyl]-2-(4-chlorophenyl)pyrimidine;
5-[[trans-4-(1E-butenyl)cyclohexyl]ethynyl]-2-(4-chlorophenyl)pyrimidine;
5-[[trans-4-(1E-propenyl)cyclohexyl]ethynyl]-2-(4-chloro-3-fluorophenyl)pyrimidine;
5-[[trans-4-(1E-butenyl)cyclohexyl]ethynyl]-2-(4-chloro-3-fluorophenyl)pyrimidine.

EXAMPLE 5

From 1.15 g of methyltriphenylphosphonium bromide, 0.37 g of potassium t-butylate and 0.44 g of 3-[trans-4-[(4'-fluoro-4-biphenylyl)ethynyl]cyclohexyl]propanal there is obtained, analogously to that described in Example 3, 4-[[trans-4-(3-butenyl)cyclohexyl]ethynyl]-4'-fluorobiphenyl.

The 3-[trans-4-[(4'-fluoro-4-biphenylyl)ethynyl]cyclohexyl]propanal used as the starting material can be obtained starting from trans-4-[(4'-fluoro-4-biphenylyl)ethynyl]cyclohexanecarboxaldehyde by carrying out the reaction sequence Wittig reaction with (methoxymethyl)triphenylphosphonium chloride/potassium t-butylate (see Example 2c) twice and hydrolyzing the resulting methoxyvinyl compound with formic acid to the homologous aldehyde (see Example 2d).

In an analogous manner there can be prepared:
4-[[trans-4-(3-butenyl)cyclohexyl]ethynyl]-3',4'-difluorobiphenyl;
4-[[trans-4-(3-butenyl)cyclohexyl]ethynyl]-4'-chlorobiphenyl;
4-[[trans-4-(3-butenyl)cyclohexyl]ethynyl]-4'-chloro-3'-fluorobiphenyl;
4-[[trans-4-(3-butenyl)cyclohexyl]ethynyl]-4'-(trifluoromethoxy)biphenyl;
4-[[trans-4-(3-butenyl)cyclohexyl]ethynyl]-4'-(difluoromethoxy)biphenyl;
5-[[trans-4-(3-butenyl)cyclohexyl]ethynyl]-2-(4-fluorophenyl)pyridine;
5-[[trans-4-(3-butenyl)cyclohexyl]ethynyl]-2-(3,4-difluorophenyl)pyridine;
5-[[trans-4-(3-butenyl)cyclohexyl]ethynyl]-2-(4-chlorophenyl)pyridine;
5-[[trans-4-(3-butenyl)cyclohexyl]ethynyl]-2-(4-chloro-3-fluorophenyl)pyridine;
5-[[trans-4-(3-butenyl)cyclohexyl]ethynyl]-2-(4-fluorophenyl)pyrimidine;
5-[[trans-4-(3-butenyl)cyclohexyl]ethynyl]-2-(3,4-difluorophenyl)pyrimidine;
5-[[trans-4-(3-butenyl)cyclohexyl]ethynyl]-2-(4-chlorophenyl)pyrimidine;
5-[[trans-4-(3-butenyl)cyclohexyl]ethynyl]-2-(4-chloro-3-fluorophenyl)pyrimidine.

When 3-[trans-4-[(4'-fluoro-4-biphenylyl)ethynyl]cyclohexyl]propanal is subjected to an additional homologization sequence Wittig reaction with (methoxymethyl)triphenylphosphonium chloride/potassium t-butylate and hydrolysis with formic acid before the final Wittig reaction with methyl triphenylphosphonium bromide/potassium t-butylate, then 4-[[trans-4-(4-pentenyl)-cyclohexyl]ethynyl]-4'-fluorobiphenyl is obtained.

In an analogous manner there can be prepared:
4-[[trans-4-(4-pentenyl)cyclohexyl]ethynyl]-3',4'-difluorobiphenyl;
4-[[trans-4-(4-pentenyl)cyclohexyl]ethynyl]-4'-chlorobiphenyl;
4-[[trans-4-(4-pentenyl)cyclohexyl]ethynyl]-4'-chloro-3'-fluorobiphenyl;
5-[[trans-4-(4-pentenyl)cyclohexyl]ethynyl]-2-(4-fluorophenyl)pyridine;
5-[[trans-4-(4-pentenyl)cyclohexyl]ethynyl]-2-(3,4-difluorophenyl)pyridine;
5-[[trans-4-(4-pentenyl)cyclohexyl]ethynyl]-2-(4-chlorophenyl)pyridine;
5-[[trans-4-(4-pentenyl)cyclohexyl]ethynyl]-2-(4-chloro-3-fluorophenyl)pyridine;
5-[[trans-4-(4-pentenyl)cyclohexyl]ethynyl]-2-(4-fluorophenyl)pyrimidine;
5-[[trans-4-(4-pentenyl)cyclohexyl]ethynyl]-2-(3,4-difluorophenyl)pyrimidine;
5-[[trans-4-(4-pentenyl)cyclohexyl]ethynyl]-2-(4-chlorophenyl)pyrimidine;
5-[[trans-4-(4-pentenyl)cyclohexyl]ethynyl]-2-(4-chloro-3-fluorophenyl)pyrimidine.

EXAMPLE 6

0.15 g of sodium hydride suspension in oil (about 55%) is washed with pentane and treated with 5 ml of tetrahydrofuran. A solution of 0.36 g of 3-[trans-4-[(4'-fluoro-4-biphenylyl)ethynyl]cyclohexyl]propanol in 5 ml of tetrahydrofuran is added dropwise and the reaction mixture is stirred for 0.5 hour before 0.2 ml of methyl iodide is added. The suspension is stirred at 62° C. for 1 hour. After cooling it is diluted with 40 ml of diethyl ether and washed neutral with water, dried over sodium sulphate and concentration. Chromatography of the residue on hexane/ethyl acetate (vol. 99:1) and recrystallization from hexane yields pure 4'-[[trans-4-(3-methoxypropyl)cyclohexyl]ethynyl]-4'-fluorobiphenyl.

The 3-[trans-4-[(4'-fluoro-4-biphenylyl)ethynyl]cyclohexyl]propanol used as the starting material can be prepared as follows:

A solution of 0.44 g of 3-[trans-4-[(4'-fluoro-4-biphenylyl)ethynyl]cyclohexyl]propanal in 20 ml of methanol/water (vol. 4:1) and 15 ml of dioxan is treated portionwise with 0.10 g of sodium borohydride. The reaction mixture is stirred at room temperature for 0.75 hour and concentrated. The residue is treated with water and extracted with diethyl ether. The ether phase is washed with water, dried over sodium sulphate, filtered and evaporated. 0.36 g of 3-[trans-4-[(4'-fluoro-4-biphenylyl)ethynyl]cyclohexyl]propanol is obtained.

EXAMPLE 7

Binary mixtures (BM) with 4-(trans-4-pentylcyclohexyl)benzonitrile were prepared in order to investigate the properties of the compounds of formula I in mixtures. The threshold potential ($V_{10}$) and the response times ($t_{on}$ and $t_{off}$) were measured at 22° C. in a TN cell (low bias tilt) with 8 μm plate separation; the 2.5-fold value of the threshold potential ($V_{10}$) was chosen as the operating voltage. The corresponding data for 4-(trans-4-pentylcyclohexyl)benzonitrile are: cl.p. (N-I) 54.6° C., $V_{10}$=1.62 V, $t_{on}$=22 ms, $t_{off}$=42 ms, Δn=0.120.

BM-1
90 wt. % of 4-(trans-4-pentylcyclohexyl)benzonitrile
10 wt. % of 4-[(trans-4-propylcyclohexyl)ethynyl]-4'-fluoro-biphenyl;
cl.p. (N-I) 61.4° C., $V_{10}$=1.58 V, $t_{on}$=28 ms, $t_{off}$=42 ms, Δn=0.132.

BM-2
80 wt. % of 4-(trans-4-pentylcyclohexyl)benzonitrile
20 wt. % of 4-[(trans-4-propylcyclohexyl)ethynyl]-4'-fluoro-biphenyl;
cl.p. (N-I) 69.9° C., $V_{10}$=1.63 V, $t_{on}$=30 ms, $t_{off}$=45 ms, Δn=0.144.

BM-3
90 wt. % of 4-(trans-4-pentylcyclohexyl)benzonitrile
10 wt. % of 4-[(trans-4-butylcyclohexyl)ethynyl]-4'-fluoro-biphenyl;
cl.p. (N-I) 61.0° C., $V_{10}$=1.60 V, $t_{on}$=28 ms, $t_{off}$=45 ms, Δn=0.130.

BM-4
90 wt. % of 4-(trans-4-pentylcyclohexyl)benzonitrile
10 wt. % of 4-[(trans-4-propylcyclohexyl)ethynyl]-3',4'-difluorobiphenyl;
cl.p. (N-I) 58.2° C., $V_{10}$=1.43 V, $t_{on}$=32 ms, $t_{off}$=45 ms, Δn=0.130.

BM-5
80 wt. % of 4-(trans-4-pentylcyclohexyl)benzonitrile
20 wt. % of 4-[(trans-4-propylcyclohexyl)ethynyl]-3',4'-difluorobiphenyl;
cl.p. (N-I) 61.4° C., $V_{10}$=1.42 V, $t_{on}$=38 ms, $t_{off}$=52 ms, Δn=0.135.

BM-6
90 wt. % of 4-(trans-4-pentylcyclohexyl)benzonitrile
10 wt. % of 4-[(trans-4-propylcyclohexyl)ethynyl]-2-(3,4-difluorophenyl)pyridine;
cl.p. (N-I) 57.5° C., $V_{10}$=1.43 V, $t_{on}$=31 ms, $t_{off}$=49 ms, Δn=0.130.

BM-7
90 wt. % of 4-(trans-4-pentylcyclohexyl)benzonitrile
10 wt. % of 4-[(trans-4-butylcyclohexyl)ethynyl]-4'-chlorobiphenyl;
cl.p. (N-I) 63.8° C., $V_{10}$=1.66 V, $t_{on}$=26 ms, $t_{off}$=46 ms, Δn=0.134.

BM-8
80 wt. % of 4-(trans-4-pentylcyclohexyl)benzonitrile
20 wt. % of 4-[(trans-4-butylcyclohexyl)ethynyl]-4'-chlorobiphenyl;
cl.p. (N-I) 73.3° C., $V_{10}$=1.72 V, $t_{on}$=29 ms, $t_{off}$=49 ms, Δn=0.142.

BM-9
90 wt. % of 4-(trans-4-pentylcyclohexyl)benzonitrile
10 wt. % of 4-[(trans-4-propylcyclohexyl)ethynyl]-4'-chloro-3'-fluorobiphenyl;
cl.p. (N-I) 60.2° C., $V_{10}$=1.56 V, $t_{on}$=30 ms, $t_{off}$=49 ms, Δn=0.132.

BM-10
80 wt. % of 4-(trans-4-pentylcyclohexyl)benzonitrile
20 wt. % of 4-[(trans-4-propylcyclohexyl)ethynyl]-4'-chloro-3'-fluorobiphenyl;
cl.p. (N-I) 65.8° C., $V_{10}$=1.60 V, $t_{on}$=33 ms, $t_{off}$=55 ms, Δn=0.138.

BM-11
90 wt. % of 4-(trans-4-pentylcyclohexyl)benzonitrile
10 wt. % of 4-[(trans-4-butylcyclohexyl)ethynyl]-4'-chloro-3'-fluorobiphenyl;
cl.p. (N-I) 59.6° C., $V_{10}$=1.55 V, $t_{on}$=29 ms, $t_{off}$=50 ms, Δn=0.130.

BM-12
80 wt. % of 4-(trans-4-pentylcyclohexyl)benzonitrile
20 wt. % of 4-[(trans-4-butylcyclohexyl)ethynyl]-4'-chloro-3'-fluorobiphenyl;
cl.p. (N-I) 63.8° C., $V_{10}$=1.53 V, $t_{on}$=39 ms, $t_{off}$=66 ms, Δn=0.137.

BM-13
80 wt. % of 4-(trans-4-pentylcyclohexyl)benzonitrile
20 wt. % of 4-[(trans-4-propylcyclohexyl)ethynyl]-2-(3,4-difluorophenyl)pyridine;
cl.p. (N-I) 60.5° C., $V_{10}$=1.34 V, $t_{on}$=40 ms, $t_{off}$=58 ms, Δn=0.137.

BM-14
90 wt. % of 4-(trans-4-pentylcyclohexyl)benzonitrile
10 wt. % of 5-[(trans-4-propylcyclohexyl)ethynyl]-2-(4-chloro-3-fluorophenyl)pyridine;
cl.p. (N-I) 60.1° C., $V_{10}$=1.49 V, $t_{on}$=27 ms, $t_{off}$=45 ms, Δn=0.134.

BM-15
80 wt. % of 4-(trans-4-pentylcyclohexyl)benzonitrile
20 wt. % of 5-[(trans-4-propylcyclohexyl)ethynyl]-2-(4-chloro-3-fluorophenyl)pyridine;
cl.p. (N-I) 65.6° C., $V_{10}$=1.47 V, $t_{on}$=37 ms, $t_{off}$=58 ms, Δn=0.146.

BM-16
90 wt. % of 4-(trans-4-pentylcyclohexyl)benzonitrile
10 wt. % of 5-[(trans-4-propylcyclohexyl)ethynyl]-2-(4-fluorophenyl)pyrimidine;
cl.p. (N-I) 62.0° C., $V_{10}$=1.56 V, $t_{on}$=29 ms, $t_{off}$=48 ms, Δn=0.133.

BM-17
80 wt. % of 4-(trans-4-pentylcyclohexyl)benzonitrile
20 wt. % of 5-[(trans-4-propylcyclohexyl)ethynyl]-2-(4-fluorophenyl)pyrimidine;
cl.p. (N-I) 69.7° C., $V_{10}$=1.56 V, $t_{on}$=30 ms, $t_{off}$=49 ms, Δn=0.144.

BM-18
90 wt. % of 4-(trans-4-pentylcyclohexyl)benzonitrile
10 wt. % of 5-[(trans-4-butylcyclohexyl)ethynyl]-2-(4-fluorophenyl)pyrimidine;
cl.p. (N-I) 61.7° C., $V_{10}$=1.54 V, $t_{on}$=27 ms, $t_{off}$=47 ms, Δn=0.131.

BM-19
80 wt. % of 4-(trans-4-pentylcyclohexyl)benzonitrile
20 wt. % of 5-[(trans-4-butylcyclohexyl)ethynyl]-2-(4-fluorophenyl)pyrimidine;
cl.p. (N-I) 69.3° C., $V_{10}$=1.51 V, $t_{on}$=32 ms, $t_{off}$=52 ms, Δn=0.141.

BM-20
90 wt. % of 4-(trans-4-pentylcyclohexyl)benzonitrile
10 wt. % of 5-[(trans-4-propylcyclohexyl)ethynyl]-2-(3,4-difluorophenyl)pyrimidine;
cl.p. (N-I) 59.1° C., $V_{10}$=1.48 V, $t_{on}$=31 ms, $t_{off}$=47 ms, Δn=0.130.

BM-21
80 wt. % of 4-(trans-4-pentylcyclohexyl)benzonitrile 20 wt. % of 5-[(trans-4-propylcyclohexyl)ethynyl]-2-(3,4-difluorophenyl)pyrimidine;

cl.p. (N-I) 63.9° C., $V_{10}$=1.45 V, $t_{on}$=32 ms, $t_{off}$=52 ms.

BM-22

90 wt. % of 4-(trans-4-pentylcyclohexyl)benzonitrile
10 wt. % of 5-[(trans-4-butylcyclohexyl)ethynyl]-2-(3,4-difluorophenyl)pyrimidine;

cl.p. (N-I) 58.9° C., $V_{10}$=1.44 V, $t_{on}$=31 ms, $t_{off}$=49 ms, $\Delta n$=0.129.

BM-23

80 wt. % of 4-(trans-4-pentylcyclohexyl)benzonitrile
20 wt. % of 5-[(trans-4-butylcyclohexyl)ethynyl]-2-(3,4-difluorophenyl)pyrimidine;

cl.p. (N-I) 63.8° C., $V_{10}$=1.41 V, $t_{on}$=34 ms, $t_{off}$=56 ms, $\Delta n$=0.135.

BM-24

90 wt. % of 4-(trans-4-pentylcyclohexyl)benzonitrile
10 wt. % of 5-[(trans-4-propylcyclohexyl)ethynyl]-2-(4-chloro-3-fluorophenyl)pyrimidine;

cl.p. (N-I) 61.3° C., $V_{10}$=1.44 V, $t_{on}$=31 ms, $t_{off}$=48 ms, $\Delta n$=0.134.

BM-25

80 wt. % of 4-(trans-4-pentylcyclohexyl)benzonitrile
20 wt. % of 5-[(trans-4-propylcyclohexyl)ethynyl]-2-(4-chloro-3-fluorophenyl)pyrimidine;

cl.p. (N-I) 67.0° C., $V_{10}$=1.47 V, $t_{on}$=35 ms, $t_{off}$=56 ms, $\Delta n$=0.147.

BM-26

90 wt. % of 4-(trans-4-pentylcyclohexyl)benzonitrile
10 wt. % of 5-[(trans-4-butylcyclohexyl)ethynyl]-2-(4-chloro-3-fluorophenyl)pyrimidine;

cl.p. (N-I) 61.3° C., $V_{10}$=1.49 V, $t_{on}$=29 ms, $t_{off}$=49 ms, $\Delta n$=0.131.

BM-27

80 wt. % of 4-(trans-4-pentylcyclohexyl)benzonitrile
20 wt. % of 5-[(trans-4-butylcyclohexyl)ethynyl]-2-(4-chloro-3-fluorophenyl)pyrimidine;

cl.p. (N-I) 69.3° C., $V_{10}$=1.47 V, $t_{on}$=33 ms, $t_{off}$=57 ms.

BM-28

90 wt. % of 4-(trans-4-pentylcyclohexyl)benzonitrile
10 wt. % of 4-[(trans-5-(1E-propenyl)-1,3-dioxan-2-yl)ethynyl]-3',4'-difluorobiphenyl;

cl.p. (N-I) 57.7° C., $V_{10}$=1.47 V, $t_{on}$=31 ms, $t_{off}$=45 ms, $\Delta n$=0.124.

BM-29

90 wt. % of 4-(trans-4-pentylcyclohexyl)benzonitrile
10 wt. % of 5-[(trans-5-propyl-1,3-dioxan-2-yl)ethynyl]-2-(3,4-difluorophenyl)pyridine;

cl.p. (N-I) 55.5° C., $V_{10}$=1.42 V, $t_{on}$=36 ms, $t_{off}$=56 ms, $\Delta n$=0.128.

BM-30

90 wt. % of 4-(trans-4-pentylcyclohexyl)benzonitrile
10 wt. % of 4-(1-hexynyl)-4'-fluorobiphenyl;

cl.p. (N-I) 44.0° C., $V_{10}$=1.30 V, $t_{on}$=31 ms, $t_{off}$=50 ms, $\Delta n$=0.121.

BM-31

80 wt. % of 4-(trans-4-pentylcyclohexyl)benzonitrile
20 wt. % of 4-(1-hexynyl)-4'-fluorobiphenyl;

cl.p. (N-I) 34.5° C., $t_{on}$=30 ms, $t_{off}$=61 ms, $\Delta n$=0.111.

BM-32

90 wt. % of 4-(trans-4-pentylcyclohexyl)benzonitrile
10 wt. % of 5-(1-hexynyl)-2-(3,4-difluorophenyl)pyridine;

cl.p. (N-I) 42.0° C., $V_{10}$=1.28 V, $t_{on}$=30 ms, $t_{off}$=50 ms, $\Delta n$=0.116.

BM-33

80 wt. % of 4-(trans-4-pentylcyclohexyl)benzonitrile
20 wt. % of 5-(1-hexynyl)-2-(3,4-difluorophenyl)pyridine;

cl.p. (N-I) 30.3° C., $V_{10}$=1.01 V, $t_{on}$=38 ms, $t_{off}$=66 ms, $\Delta n$=0.099.

BM-34

90 wt. % of 4-(trans-4-pentylcyclohexyl)benzonitrile
10 wt. % of 5-(1-pentynyl)-2-(4-chloro-3-fluorophenyl)pyridine;

cl.p. (N-I) 47.0° C., $V_{10}$=1.35 V, $t_{on}$=29 ms, $t_{off}$=47 ms, $\Delta n$=0.126.

BM-35

80 wt. % of 4-(trans-4-pentylcyclohexyl)benzonitrile
20 wt. % of 5-(1-pentynyl)-2-(4-chloro-3-fluorophenyl)pyridine;

cl.p. (N-I) 39.5° C., $V_{10}$=1.16 V, $t_{on}$=34 ms, $t_{off}$=56 ms, $\Delta n$=0.128.

BM-36

90 wt. % Of 4-(trans-4-pentylcyclohexyl)benzonitrile
10 wt. % of 5-(1-pentynyl)-2-(3,4-difluorophenyl)-pyrimidine;

cl.p. (N-I) 46.2° C., $V_{10}$=1.31 V, $t_{on}$=28 ms, $t_{off}$=45 ms, $\Delta n$=0.124.

BM-37

80 wt. % of 4-(trans-4-pentylcyclohexyl)benzonitrile
20 wt. % of 5-(1-pentynyl)-2-(3,4-difluorophenyl)-pyrimidine;

cl.p. (N-I) 38.9° C., $V_{10}$=1.11 V, $t_{on}$=31 ms, $t_{off}$=49 ms, $\Delta n$=0.123.

BM-38

90 wt. % of 4-(trans-4-pentylcyclohexyl)benzonitrile
10 wt. % of 5-(1-hexynyl)-2-(3,4-difluorophenyl)-pyrimidine;

cl.p. (N-I) 44.4° C., $V_{10}$=1.26 V, $t_{on}$=31 ms, $t_{off}$=49 ms, $\Delta n$=0.120.

BM-39

80 wt. % of 4-(trans-4-pentylcyclohexyl)benzonitrile
20 wt. % of 5-(1-hexynyl)-2-(3,4-difluorophenyl)-pyrimidine;

cl.p. (N-I) 35.4° C., $V_{10}$=1.15 V, $t_{on}$=28 ms, $t_{off}$=55 ms, $\Delta n$=0.115.

BM-40

90 wt. % of 4-(trans-4-pentylcyclohexyl)benzonitrile
10 wt. % of 5-(1-hexynyl)-2-(4-fluorophenyl)pyrimidine;

cl.p. (N-I) 47.0° C., $V_{10}$=1.35 V, $t_{on}$=27 ms, $t_{off}$=43 ms, $\Delta n$=0.124.

BM-41

80 wt. % of 4-(trans-4-pentylcyclohexyl)benzonitrile
20 wt. % of 5-(1-hexynyl)-2-(4-fluorophenyl)pyrimidine;

cl.p. (N-I) 40.2° C., $V_{10}$=1.20 V, $t_{on}$=29 ms, $t_{off}$=48 ms, $\Delta n$=0.125.

BM-42

90 wt. % of 4-(trans-4-pentylcyclohexyl)benzonitrile
10 wt. % of 5-(1-pentynyl)-2-(4-chloro-3-fluorophenyl)pyrimidine;

cl.p. (N-I) 48.1° C., $V_{10}$=1.36 V, $t_{on}$=27 ms, $t_{off}$=44 ms, $\Delta n$=0.125.

BM-43

80 wt. % of 4-(trans-4-pentylcyclohexyl)benzonitrile
20 Wt. % of 5-(1-pentynyl)-2-(4-chloro-3-fluorophenyl)pyrimidine;

cl.p. (N-I) 44.1° C., $V_{10}$=1.20 V, $t_{on}$=30 ms, $t_{off}$=50 ms, $\Delta n$=0.127.

BM-44

90 wt. % of 4-(trans-4-pentylcyclohexyl)benzonitrile

10 Wt. % of 4-(trans-4-propylcyclohexyl)ethynyl]-4'-difluoromethoxy)3',5'-difluorobiphenyl;
cI.p. (N-I) 57.6° C., $V_{10}=1.58$ V, $t_{on}=29$ ms, $t_{off}=50$ ms, $\Delta n=0.128$.

BM-45
80 wt. % of 4-(trans-4-pentylcyclohexyl)benzonitrile
20 Wt. % of 4-(trans-4-propylcyclohexyl)ethynyl]-4'-difluoromethoxy)-3',5'-difluorobiphenyl;
cI.p. (N-I) 60.9° C., $V_{10}=1.51$ V, $t_{on}=35$ ms, $t_{off}=59$ ms, $\Delta n=0.134$.

We claim:

1. A compound of the formula

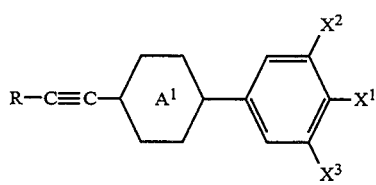

wherein
R is an alkyl group with 1 to 12 carbon atoms or a group of

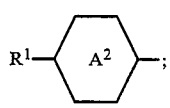

ring $A^1$ is 1,4-phenylene, which is unsubstituted or substituted with one fluorine atom, pyridine-2,5-diyl or pyrimidine-2,5-diyl;
ring $A^2$ is trans-1,4-cyclohexylene or trans-1,3-dioxane-2,5-diyl;
$R^1$ is an alkyl group with 1 to 12 or an alkenyl or alkoxyalkyl group with 2 to 12 carbon atoms;
$X^1$ is fluorine, chlorine, or bromine and can also be trifluoromethyl, trifluoromethoxy or difluoromethoxy when R is an alkyl group with 1 to 12 carbon atoms, when ring $A^1$ is 1,4-phenylene substituted with one fluorine atom, pyridine-2,5-diyl or pyrimidine-2,5-diyl, when ring $A^2$ is trans-1,3-dioxane-2,5-diyl, or when $X^2$ or $X^3$ is fluorine; and
$X^2$, $X^3$ each independently is hydrogen or fluorine.

2. A compound according to claim 1 of the formula

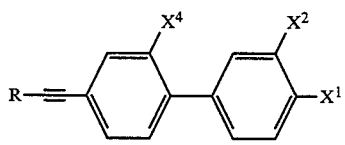

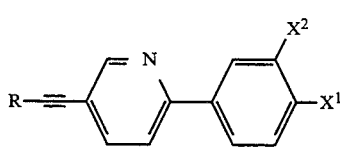

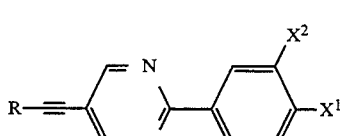

wherein R is an alkyl group with 1 to 12 carbon atoms; $X^4$ is hydrogen or fluorine and $X^1$ and $X^2$ each independently is hydrogen or fluorine.

3. A compound according to claim 1 of the general formulas

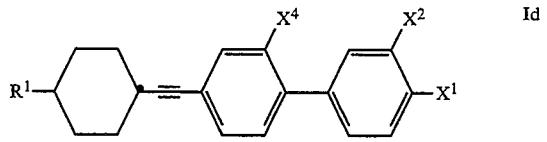

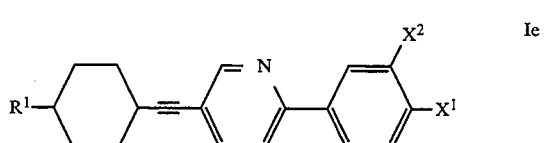

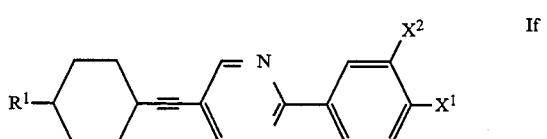

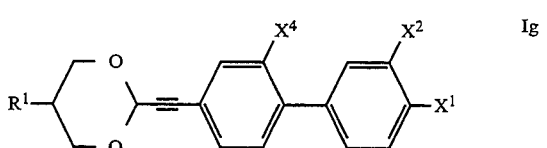

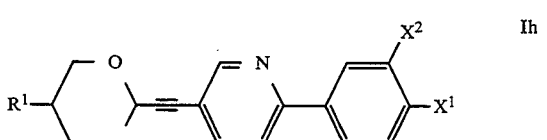

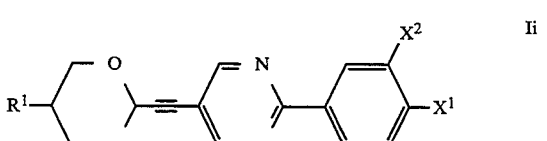

wherein $R^1$, $X^1$ and $X^2$ are as defined in claim 1 and $X^4$ is hydrogen or fluorine.

4. A compound according to claim 1, wherein R is alkyl with 1 to 7 carbon atoms and $R^1$ is alkyl with 1 to 7 carbon atoms or alkenyl or alkoxyalkyl with 2 to 7 carbon atoms.

5. A compound according to claim 4, wherein R is an alkyl group with 2 to 5 carbon atoms.

6. A compound according to claim 3, wherein $R^1$ is alkyl or alkenyl with 2 to 5 carbon atoms and $A^2$ is trans-1,4-cyclohexylene.

7. The compound of claim 6 which is 4-[trans-4-propylcyclohexyl)ethynyl]-4'-fluorophenyl.

8. A compound according to claim 1 wherein $A^2$ is trans-1,3-dioxane-2,5-diyl.

9. The compound of claim 8 which is 5-[(trans-5-propyl-1,3-dioxan-2-yl)ethynyl]-2-(3,4-difluorophenyl)-pyridine.

10. The compound of claim 6 which is 4-[(trans-4-vinylcyclohexyl)ethynyl]-4'-fluorobiphenyl.

11. The compound of claim 6 which is 4-[trans-4-(1E-propenylcyclohexyl)ethynyl]-4'-fluorobiphenyl.

12. The compound of claim 6 which is 4-[[trans-4-(3-butenyl)cyclohexyl]ethynyl]-4'-fluorobiphenyl.

13. The compound of claim 6 which is 4-[[trans-4-(4-pentenyl)cyclohexyl]ethynyl]-4'-fluorobiphenyl.

14. A compound of claim 4 wherein $R^1$ is alkoxyalkyl with 2 to 7 carbon atoms.

15. The compound of claim 14 which is 4'-[[trans-4-(3-methoxypropyl)cyclohexyl]ethynyl]-4'-fluorobiphenyl.

16. A liquid crystalline mixture comprising at least two components, wherein at least one component is a compound of the formula

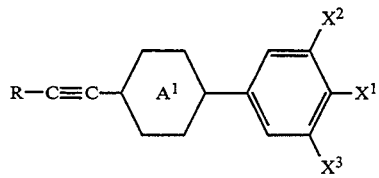

wherein

R is an alkyl group with 1 to 12 carbon atoms or a group of the formula

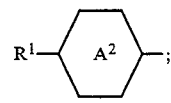

ring $A^1$ is 1,4-phenylene, which is unsubstituted or substituted with one fluorine atom, pyridine-2,5-diyl or pyrimidine-2,5-diyl;

ring $A^2$ is trans-1,4-cyclohexylene or trans-1,3-dioxane-2,5diyl;

$R^1$ is an alkyl group with 1 to 12 or an alkenyl or alkoxyalkyl group with 2 to 12 carbon atoms;

$X^1$ is fluorine, chlorine, or bromine and can also be trifluoromethyl, trifluoromethoxy or difluoromethoxy when R is an alkyl group with 1 to 12 carbon atoms, when ring $A^1$ is 1,4-phenylene substituted with one fluorine atom, pyridine-2,5-diyl or pyrimidine-2,5-diyl, when ring $A^2$ is trans-1,3-dioxane-2,5-diyl, or when $X^2$ or $X^3$ is fluorine; and $X^2$, $X^3$ each independently is hydrogen or fluorine.

* * * * *

UNITED STATES PATENT AND TRADEMARK OFFICE
CERTIFICATE OF CORRECTION

PATENT NO. : 5,447,657
DATED : September 5, 1995
INVENTOR(S) : Martin Schadt, Alois Villiger It is certified that error appears in the above-identified patent and that said Letters Patent is hereby corrected as shown below:

Claim 1, Column 27, line 25: "R is an alkyl group with 1 to 12 carbon atoms or a group of" should read --- R is an alkyl group with 1 to 12 carbon atoms or a group of the formula --- .

Claim 16, Column 30, lines 10-11: "ring $A^2$ is trans-1,4-cyclohexylene or trans-1,3-dioxane-2,5diyl" should read --- ring $A^2$ is trans-1,4-cyclohexylene or trans-1,3-dioxane-2,5-diyl --- .

Signed and Sealed this

Ninth Day of January, 1996

Attest:

BRUCE LEHMAN

*Attesting Officer*    Commissioner of Patents and Trademarks